US005639607A

United States Patent [19]
Desnick et al.

[11] Patent Number: 5,639,607
[45] Date of Patent: Jun. 17, 1997

[54] METHOD AND KITS FOR DETECTING A POLYMORPHISM IN δ-AMINOLEVULINATE DEHYDRATASE GENE WHICH IS ASSOCIATED WITH AN ALTERED SUSCEPTIBILITY TO LEAD POISONING

[75] Inventors: Robert J. Desnick, New York; James G. Wetmur, Scarsdale, both of N.Y.

[73] Assignee: Mount Sinai School of Medicine of the City University of New York, New York, N.Y.

[21] Appl. No.: 195,744

[22] Filed: Feb. 14, 1994

Related U.S. Application Data

[63] Continuation of Ser. No. 742,130, Aug. 7, 1991, abandoned.
[51] Int. Cl.$^6$ .............................. C12Q 1/68; C12P 19/34; C07H 21/04
[52] U.S. Cl. .................. 435/6; 435/91.2; 536/24.33; 935/77; 935/78
[58] Field of Search ........................ 435/6, 91.2, 195; 536/23.2, 23.5, 24.33, 24.31

[56] References Cited

U.S. PATENT DOCUMENTS 4,683,195   7/1987   Mullis et al. ..................... 435/91

OTHER PUBLICATIONS

Seppalainen et al., "Early Neurotoxic Effects of Occupational Lead Exposure: A Prospective Study", Neurotoxicology, 4:181–192 (1983).
Needleman et al., "Deficits in Psychologic and Classroom Performance of Children With Elevated Dentine Lead Levels", N. Engl. J. Med., 300:689–695 (1979).
Baker et al., "Occupational Lead Neurotoxicity: Improvement in Behavioural Effects After Reduction of Exposure", Brit. J. Industr. Med., 42: 507–516 (1985).
Jeyaratnam et al., "Neuropsychological Studies on Lead Workers in Singapore", Brit. J. Industr. Med., 43:626–629 (1987).
Lilis et al., "Effects of Low–Level Lead and Arsenic Exposure on Copper Smelter Workers", Arch. Env. Health, 40:38–47 (1985).
Winneke et al., "Neuropsychological Comparison of Children With Different Tooth–Lead Levels. Preliminary Report", Internat. Conf. on Heavy Metals in the Environment, Geneva, World Health Organization, pp. 553–556 (1981).
Smith et al., "The Effects of Lead Exposure on Urban Children: The Institute of Child Health/Southampton Study", Dev. Med. Child Neurol., 47:1–54 (1983).
Bellinger et al., "Longitudinal Analyses of Prenatal and Postnatal Lead Exposure and Early Cognitive Development", N. Engl. J. Med., 316:1037–1043 (1987).
Needleman et al., "The Long–Term Effects of Exposure to Low Doses of Lead in Childhood", N. Engl. J. Med., 322:83–88 (1990).
Gerber et al., "Toxicity, Mutagenicity and Teratogenicity of Lead", Mutat. Res., 76:115–141 (1980).
Wibberley et al., "Lead Levels in Human Placentae from Normal and Malformed Births", J. Med. Genet., 14:339–345 (1977).
Needleman et al., "The Relationship Between Prenatal Exposure to Lead and Congenital Anomalies", J. Amer. Med. Assoc., 251:2956–2959 (1984).

(List continued on next page.)

*Primary Examiner*—Lisa B. Arthur
*Attorney, Agent, or Firm*—Brumbaugh, Graves, Donohue & Raymond

[57] ABSTRACT

A method is disclosed for detecting a polymorphism in the δ-aminolevulinate dehydratase gene which is associated with an altered susceptibility to lead poisoning. A point mutation which generates an MspI restriction endonuclease recognition site was found in the ALAD2 allele of the δ-aminolevulinate dehydratase gene which is not present in the ALAD1 allele. Kit containing primers for the amplification of the polymorphic region of the ALAD gene are provided.

10 Claims, 1 Drawing Sheet

PCR Method for the *MspI* Polymorphism

OTHER PUBLICATIONS

Deknudt et al., "Chromosome Aberrations Observed in Male Workers Occupationally Exposed to Lead", Environ. Physiol. Biochem., 3:132–138 (1973).

Wu et al., "The Quaternary Structure of δ–Aminolevulinic Acid Dehydratase from Bovine Liver", Proc. Natl. Acad. Sci. USA, 71: 1767–1770 (1974).

Gurne et al., "Dissociation and Reassociation of Immobilized Porphobilinogen Synthase: Use of Immobilized Subunits for Enzyme Isolation", Proc. Natl. Acad. Sci. USA, 74:1383–1388 (1977).

Anderson and Desnick, "Purification and Properties of δ–Aminole–vulinate Dehydrase from Human Erythrocytes", J. Biol. Chem., 254: 6924–6930 (1979).

Bevan et al., "Mechanism of Porphobilinogen Synthase", J. Biol. Chem., 255:2030–2035 (1980).

Tsukamoto et al., "The Role of Zinc With Special Reference to the Essential Thiol Groups in δ–Aminolevulinic Acid Dehydratase of Bovine Liver", Biochem. Biophys. Acta., 570:167–178 (1979).

Tsukamoto et al., "Zinc and Cysteine Residues in the Active Site of Bovine Liver δ–Aminolevulinic Acid Dehydratase", Int. J. Biochem., 12:751–756 (1980).

Jaffe et al., "Porphobilinogen Synthase Modification with Methyl–methanethiosulfonate", J. Biol. Chem., 259:5032–5036 (1984).

Jordan et al., "Mechanism of Actionof 5–aminolaevulinate dehydratase from Human Erythrocytes", Biochem. J., 227:1015–1020 (1985).

Morgan and Burch, "Comparative Tests for Diagnosis of Lead Poisoning", Arch. Intern. Med., 130:335–340 (1972).

Chisholm, "Chronic Lead Intoxication in Children", Dev. Med. Child Neurol., 7:529–536 (1965).

Petrucci et al., "The Genetic Polymorphism of δ–Aminolevulinate Dehydrase in Italy", Hum. Genet., 60:289–290 (1982).

Battistuzzi et al., "δ–aminolevulinate Dehydrase: A New Genetic Polymorphism in Man", Ann. Hum. Genet., 45:223–229 (1981).

Potluri et al., "Human δ–Aminolevulinate Dehydratase: Chromosomal Localization to 9q34 by in situ Hybridization", Hum. Genet., 76:236–239 (1987).

Benkmann et al., "Polymorphism of Delta–Aminolevulinic Acid Dehydratase in Various Populations", Hum. Hered., 33:62–64 (1983).

Propping, Pharmacogenetics, J. Physiol. Biochem. Pharmacol., 83: 124–173 (1978).

Ziemsen et al., "Polymorphism of delta–Aminolevulinic Acid Dehydratase in Lead–Exposed Workers", Int. Arch. Occup. Environ. Health, 58:245–247 (1986).

Ben-Ezzer et al., "Genetic Polymorphism of Delta–Aminolevulinate Dehydrase in Several Population Groups in Israel", Hum. Hered., 37:229–232 (1987).

Conner et al., "Detection of Sickle Cell $^S$–Globin Allele by Hybridization with Synthetic Oligonucleotides", Proc. Natl. Acad. Sci. USA, 80:278–282 (1983).

Saiki et al., "Analysis of Enzymatically Amplified –Globin and HLA–DQ DNA with Allele–Specific Oligonucleotide Probes", Nature, 324:163–166 (1986).

Chehab et al., "Detection of Sickle Cell Anaemia and Thalassaemias", Nature, 329:293–294 (1987).

Landegren et al., "A Ligase–Mediated Gene Detection Technique", Science, 241:1077–1080 (1988).

Wu et al., "Allele–Specific Enzymatic Amplification of –globin Genomic DNA for Diagnosis of Sickle Cell Anemia", Proc. Natl. Acad. Sci. USA, 86:2757–2760 (1989).

Wu and Wallace, "The Ligation Amplification Reaction (LAR)—Amplification of Specific DNA Sequences Using Sequential Rounds of Template–Dependent Ligation", Genomics, 4:560–569 (1989).

Gordon and Ruddle, "Gene Transfer into Mouse Embryos: Production of Transgenic Mice by Pronuclear Injection", Methods Enzymol. 101: 411–432 (1983).

Southern, "Detection of Specific Sequences Among DNA Fragments Seperated by Gel Electrophoresis", J. Mol. Biol., 98: 503–517 (1975).

Saiki et al., "Primer–Directed Enzymatic Amplification of DNA with a Thermostable DNA Polymerase", Science, 239:487–491 (1988).

Kushner, "An Improved Method for Transformation of Escherichia col; with Col El Derived Plasmids", Genetic Engineering, Boyer, Nicosia, eds. Elsevier/North–Hollad Biomedical Press, Amsterdam, pp. 17–23 (1978).

Botstein et al., "Construction of a Genetic Linkage Map in Man Using Restriction Fragment Length Polymorphisms", Am. J. Hum. Genet., 32:314–331 (1980).

Pasvol et al., "Cellular Mechanism for the Protective Effect of Haemoglobin S against P. falciparum Malaria", Nature, 274:7801–7803 (1978).

Astrin et al., "—Aminolevulinic Acid Dehydratase Isozymes and Lead Toxicity", Ann. N.Y. Acad. Sci., 514:23–29 (1987).

Wetmur et al., "Human –aminolevulinate Dehydratase: Nucleotide Sequence of a Full–length cDNA Clone", Proc. Natl. Acad. Sci. USA, 83:7703–7707 (1986).

Chirgwin et al., "Isolation of Biologically Active Ribonucleic Acid From Sources Enriched in Ribonuclease", Biochem., 18:5294–5299 (1979).

Wong et al., "Branch capture reaction: displacers derived from asymmetric PCR", Nucleic Acids Research, vol. 19 No. 9, pp. 2251–2259 (May 11, 1991).

Bishop, T. R. et al., "Nucleotide sequence of rat liver δ–aminolevulinic acid dehydratase cDNA", Nucleic Acids Res. (1986), 14:10115.

Bishop, T.R. et al., "Cloning and sequence of mouse erythroid δ–aminolevulinate deyhydratase cDNA", Nucleic Acids Res. (1989), 14:1775.

Chisolm, J.J., Jr. et al., "Erythrocyte Porphobilinogen Synthase Activity as an Indicator of Lead Exposure in Children", Clin. Chem. (1985), 31/4:601–605.

Claudio, Luz et al., "Increased Vesicular Transport and Decreased Mitochondrial Content in Blood–Brain Barrier Endothelial Cells During Experimental Autoimmune Encephalomyelitis", Amer. J. path. (1989), 135/6:1157–1168.

Jaffe, E.K., et al., "Reevalution of a Sensitive Indicatior of Early Lead Exposure", Biol. Trace Element Res. (1991), 28:223–231.

Wetmur, J.G. et al., "Molecular Characterization of the Human δ–Aminolevulinate Dehydratase 2 (ALAD$^2$) Allele: Implications for Molecular Screening of Individuals for Generic Susptibility to Lead Poisoning", Am. J. Hum. Genet. (1991), 49:757–763.

Wetmur, J.G. et al., "The δ–Aminolevulinate Dehydratase Polymorphism: Higher Blood Lead Levels in Lead Workers and Environmentally Exposed Children with the 1–2 and 2–2 Isozymes", Environ. Res. (1991), 56:109–119.

Smith et al., Experimental Health Perspectives, (1995) 103(3):248–253.

METHOD AND KITS FOR DETECTING A POLYMORPHISM IN δ-AMINOLEVULINATE DEHYDRATASE GENE WHICH IS ASSOCIATED WITH AN ALTERED SUSCEPTIBILITY TO LEAD POISONING

This application is a continuation of application Ser. No. 07/742,130, filed on Aug. 7, 1991 now abandoned.

FIELD OF THE INVENTION

This invention relates to a method for determining susceptibility to lead poisoning by assaying for a polymorphism in the gene encoding δ-amino levulinate dehydratase (ALA-D), as well as a diagnostic kit for determining the polymorphism comprising a means for extracting a DNA sample and a means for detecting the presence of the ALA-D polymorphism in the DNA sample.

BACKGROUND OF THE INVENTION

Lead is toxic to numerous organ systems, including the reticuloendothelial and nervous systems. The most important consequence of low-level lead toxicity is irreversible neurological damage. Although ambient lead levels are markedly below those of a decade ago as a result of the reduced use of leaded gasoline, there remain the problems of widespread detection of lead-paint poisoning of children, control of lead exposure in the workplace, increased lead absorption and low-level lead toxicity.

Recent neuroepidemiologic studies have demonstrated peripheral neurological abnormalities in lead-exposed adults at levels of 30–40 μg/dl and in children at blood lead levels as low as 20–30 μg/dl. Seppalainen et al. (1983) Neurotoxicology, 4:181–192; and Needleman et al. (1979) N. Eng. J. Med., 300:689–695. The Second National Health and Nutrition Examination Survey (NHANES-II) found that 1.5 million preschool children had blood lead levels of 25 μg/dl and above, indicating lead absorption.

Recent evidence indicates that the prevalence of central neurological symptoms is elevated and neurobehavioral performance is impaired in adults at blood lead levels of 40–60 μg/dl. Baker et al. (1985) Brit. J. Industr. Med., 41:507–516; Jeyarathnam et al. (1987) Brit. J. Industr. Med., 43:626–629; and Lilis et al. (1985) Arch. Env. Health, 40:38–47. Central nervous system dysfunction in children with elevated blood lead levels has been measured using verbal I.Q. test scores. In one U.S. study, children with blood lead levels of 25–45 μg/dl scored 4.5 points lower on the I.Q. tests after adjusting for parental education, childhood illnesses and socioeconomic status. Needleman et al. (1979). In two cross-sectional European studies, similar effects of low-level lead central nervous system toxicity were observed. Winneke et al. (1981) Internat. Conf. on Heavy Metals in the Environment, Geneva, World Health Organization, pp. 553–556; and Smith et al. (1983) Dev. Med. Child Neurol., 25(suppl 47):1–20. Furthermore, both decreases in intelligence and shortened attention span have been reported in young children who had moderately elevated umbilical cord blood lead levels at birth. Bellinger et al. (1987) N. Engl. J. Med., 316:1037–1043. By all measurements, children appear to be at significant risk from low-level lead exposure. Needleman et al., (1990) N. Engl. J. Med., 322:83–88.

In a rat model, lead has been shown to be mobilized from maternal stores during pregnancy and to cross the placenta. Moreover, lead has been shown to produce neural tube defects in three rodent species. Gerber et al. (1977) Mutat. Res., 76:115–141. In man, increased placental lead concentrations have been reported in stillborns and in infants with mental retardation and congenital anomalies. Wibberly et al. (1977) J. Med. Genet., 14:339–345. A study of over 5000 births with 3% congenital malformations demonstrated a significant dose-related correlation between placental lead concentration and congenital anomalies. Needleman et al. (1984) J. Amer. Med. Assoc., 251:2956–2959. The effects of other possible teratogenic variables were eliminated by multivariant analysis.

There is also evidence that lead affects the male gamete. Increased numbers of chromosomal aberrations in sperm have been found both in experimental animals exposed to lead and in lead workers. Deknudt et al. (1973) Environ. Physiol. Biochem., 3:132–138. Lead was one of only three substances included on the initial California "short list" of reproductive toxins. Baum. Chem. Eng. News, Mar. 16, 1987, p. 22.

ALA-D, the second enzyme in the heme biosynthetic pathway, catalyzes the asymmetric condensation of two molecules of 5-aminolevulinate (ALA) to form the monopyrrole, porphobilinogen (PBG), the precursor of heme, cytochromes and cobalamins. The mammalian enzyme has been purified to homogeneity from bovine liver and human erythrocytes. Wu et al. (1974) Proc. Natl. Acad. Sci. USA, 71:1767–1770; Gurne et al. (1977) Proc. Natl. Acad. Sci. USA, 74:1383–138; and Anderson and Desnick (1979) J. Biol. Chem., 254:6924–6930. ALA-D is a metalloenzyme composed of eight identical subunits and eight zinc atoms. Anderson and Desnick (1979); Bevan et al. (1980) J. Biol. Chem., 255:2030–2035; Tsukamoto et al. (1979) Biochem. Biophys. Acta, 570:167–178; Tsukamoto et al. (1980) Int. J. Biochem., 12:751–756; and Jaffe et al. (1984) J. Biol. Chem., 259:5032–5036.

ALA-D activity is inhibited by lead and various heavy metals as well as by the oxidation of critical thiol groups. Anderson & Desnick (1979); and Jordan et al. (1985) Biochem. J., 222:1015–1020. Lead atoms replace the zinc atoms which are required to maintain ALA-D activity. Tsukamoto et al. (1979). The inhibition of erythrocyte ALA-D activity has been used as a sensitive diagnostic indicator of lead exposure. Morgan et al. (1972) Arch. Intern. Med., 130:335–341. The inhibition is stoichiometric; e.g., 15 and 30 μg of Pb per dl blood results in 50% and 75% ALA-D inhibition, respectively. More recently, the ratio of ALA-D present before and after reactivation with zinc and DTT has been shown to correlate best to blood lead levels. Chisholm et al. (1985), Clin. Chem., 31:662–668. The inhibition of ALA-D activity results in a proportionate accumulation of ALA blood and urine. The accumulation of ALA has been causally related to the neurological manifestations of lead poisoning.

Human ALA-D, has been shown to be a polymorphic enzyme. Petrucci et al. (1982) Hum. Genet., 60:289–290; and Battistuzzi et al. (1981) Ann. Hum. Genet., 45:223–229. The allelic polypetides are encoded by a gene located on chromosome 9 in the region 9q34. Potluri et al. (1987) Hum. Genet., 76:236–239. The ALA-D gene has two common alleles, ALA-D$^1$ and ALA-D$^2$, which result in a polymorphic enzyme system with three distinct charge isozyme phenotypes, designated ALA-D 1-1, ALA-D 1-2 and ALA-D 2-2. The isozymes may be separated by starch gel electrophoresis. Battistuzzi (1981). In the Italian population, the frequencies of the isozyme phenotypes are 1-1 (81%), 1-2 (17%) and 2-2 (2%), consistent with gene frequencies of 0.90 and 0.10 for the ALA-D$^1$ and ALA-D$^2$ alleles, respectively. Similar results were obtained in other European populations, whereas expression of the ALA-D$^2$ allele was not observed in a large sample of Black individuals from Liberia. Benkmann et al. (1983) Hum. Hered., 33:62–64. A study of ALA-D isozyme phenotypes in erythrocytes of over 950 normal Caucasian individuals from New York showed the frequencies of the ALA-D 1-1, 1-2, and 1-2 isozyme phenotypes to be similar to those observed in the Italian population.

The occurrence of the ALA-D polymorphism is of interest, particularly with respect to the possible increased susceptibility of certain isozyme phenotypes to the detrimental effects of lead exposure. Polymorphisms at other genetic loci are known to be related to differential inherited responses to environmental challenges. For example, the response to Plasmodium (malaria) is affected by hemoglobin S, hemoglobin AS heterozygotes being more resistant to disease than individuals with normal hemoglobin AA. Pasval et al. (1978) Nature, 274:7801–7803. Similarly, Asian individuals are more susceptible to alcohol intoxication due to the presence of a particular alcohol dehydrogenase polymorphism. Propping (1978) J. Physiol. Biochem. Pharmacol., 83:124–173.

The existence of this common ALA-D polymorphism and the fact that ALA-D is markedly inhibited by lead suggests that there is a physiologic relationship between the frequency of the ALA-$D^2$ allele and lead poisoning. For instance, individuals with the ALA-$D^2$ allele may be more susceptible to the detrimental effects of lead exposure if the ALA-$D^2$ subunit bound lead more tightly than the ALA-$D^1$ subunit. They would have higher blood and bone lead concentrations as well as higher total body lead stores, making them even more likely to express subclinical and clinical manifestations of chronic low level or acute lead exposure. Alternatively, the tight binding of blood lead by erythrocyte ALA-$D^2$ may prevent the distribution of lead to the neurologic system, thereby preventing or minimizing the neurotoxic effects of lead.

A study of blood lead levels and ALA-D isozyme types in 1277 blood samples obtained from the New York City Lead Screening Program was performed in a double-blind fashion. That is, the blood lead levels were provided by the Toxicology Laboratory only after the blind determination of the ALA-D isozyme phenotype. Table I is a compilation of the number of individuals with the ALA-D 1-1, ALA-D 1-2, ALA-D 2-2 phenotypes having blood lead levels above or below either 25 or 30 µg/dl. These results demonstrate that a high proportion of these individuals with high blood lead levels had the ALA-$D^2$ allele. Astrin et al. (1987) Ann. N. Y. Acad. Sci., 514:23–29. The presence of the ALA-$D^2$ allele apparently leads to approximately a two-fold increase in lead retention at blood levels of 25 or 30 µg/dl. In some cases, the ethnic group was known. The incidence of the ALA-$D^2$ allele among lead poisoned Black children was high even though the incidence of the ALA-$D^2$ allele among Blacks in general is low. The results obtained support a relationship between the ALA-$D^2$ allele and the accumulation of lead in the blood. Similar data support the identical conclusion. Ziemsen et al. (1986) Int. Arch. Occup. Environ. Health, 58:245–247.

TABLE 1

HUMAN ALA-D POLYMORPHISM: ASSOCIATION WITH LEAD POISONING

| Sample Set | Blood Lead Level (µg/dl) | Total | ALA-D Isozyme Phenotype (Number and Percent in Sample Set) | | | |
|---|---|---|---|---|---|---|
| | | | 1-1 | (%) | 1-2 or | 2-2 |
| Total: | <25 | 870 | 803 | (71) | 67 | (47) |
| | ≧25 | 408 | 333 | (29) | 75 | (53) |
| | | 1278 | 1136 | (100) | 142 | (100) |
| | <30 | 1000 | 919 | (81) | 81 | (57) |
| | ≧30 | 278 | 217 | (19) | 60 | (43) |
| | | 1278 | 1136 | (100) | 142 | (100) |
| Blacks: | <30 | 292 | 282 | (88) | 10 | (38) |
| | ≧30 | 53 | 37 | (12) | 16 | (62) |
| | | 345 | 319 | (100) | 26 | (100) |

It has previously been found that the frequency of the ALA-$D^2$ allele to be 10–11% in Italian and German populations. Battistuzzi et al. (1981) "δ-aminolevulinate Dehydratase: A new Genetic Polymorphism in Man", Ann. Hum. Genet., 45:223–229; and Benkmann et al., (1983) "Polymorphism of Delta-aminolevulinic Acid Dehydratase in Various Populations", Hum. Hered., 33:62–64. A study indicated an ALA-$D^2$ allele frequency of 20% in Eastern European Ashkenazi Jews living in Israel. Ben-Ezzer et al., (1987) "Genetic Polymorphism of Delta-aminolevulinate Dehydratase in Several Population Groups in Israel", Hum. Hered., 37:229–232. The blood samples used for this study came from a Tay-Sachs screening program, which would be biased toward an Ashkenazi Jewish population. In this experiment the observed ALA-$D^2$ allele frequency of 12% was thus somewhat higher than the average frequency of 10–11% in European populations.

It would be useful to have a rapid, inexpensive diagnostic method to detect the human ALA-D polymorphism. Such a method is useful in screening for persons susceptible to lead poisoning so that they could be given jobs with less exposure to lead. Also, screening may identify children who are more susceptible to lead poisoning and therefore dictate a more rigorous prevention program, monitoring and/or detoxification therapy in such children.

SUMMARY OF THE INVENTION

A diagnostic method for determining susceptibility to lead poisoning by obtaining a biological sample from a patient and analyzing the sample for the presence of a polymorphism of the δ-amino levulinate dehydratase gene. Suitable analysis methods include but are not limited to digesting the DNA with a restriction endonuclease that recognizes the DNA sequence at the site of the polymorphism being able to cleave at the site in the ALA-$D^2$ but not the ALA-$D^1$ allele, and determining whether the DNA sample has been cleaved by the restriction endonuclease. The DNA encoding ALA-D may be amplified prior to restriction endonuclease cleavage.

The invention is useful for screening biological samples with a high degree of reliability and specificity. Samples include but are not limited to body fluids such as blood, sera, and tissue samples. A diagnostic kit is provided to perform the method of the present invention. The kit provides a means for extracting DNA from the sample, means for digesting the DNA and a means for analyzing the digestion products. A means for amplifying the DNA encoding ALA-D or a portion thereof may also be provided.

DETAILED DESCRIPTION OF THE INVENTION

Figure 1:
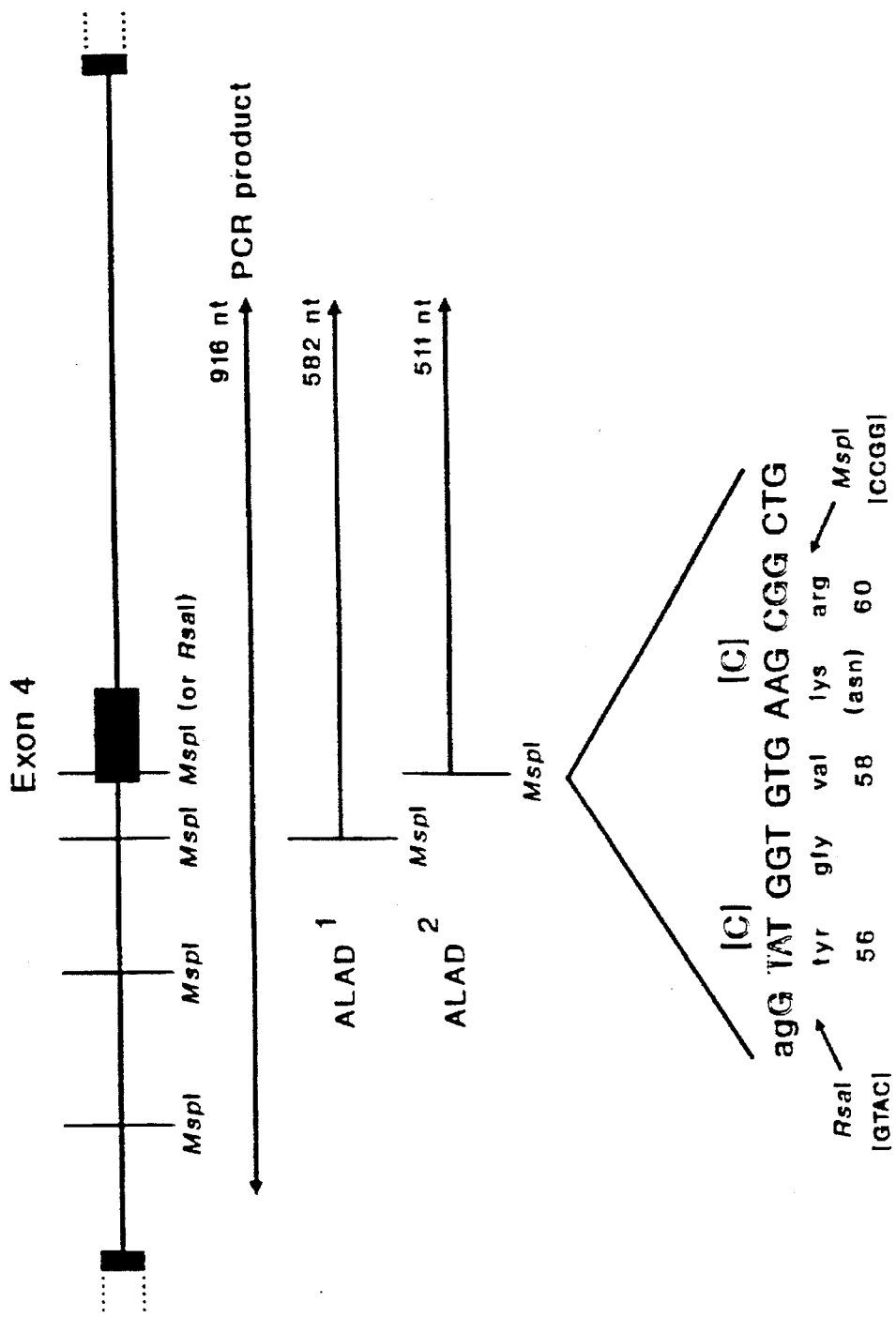
FIG. 1 shows a schematic for the PCR analysis of the ALA-D polymorphism.

The molecular nature of the ALA-D polymorphism has now been determined to be based upon the single nucleotide difference found between the sequences of the ALA-D[1] and ALA-D[2] cDNA clones. Codon 59 is AAG (lysine) in ALA-D[1] and AAC (asparagine) in ALA-D[2]. This transversion results in a new restriction endonuclease site CCGG in ALA-D[2] cDNA and in ALA-D[2] genomic DNA thus allowing differential restriction endonuclease digestion. A particularly suitable restriction endonuclease for use in the present invention is Msp I, however, any restriction endonuclease capable of recognizing the nucleotides CCGG or a DNA sequence containing the nucleotides CCGG so as to cleave the DNA at the CCGG site or any other detectable site upon recognition of CCGG is suitable for use in the present invention. The segment of DNA encoding ALA-D or a segment thereof may be amplified prior to restriction by the endonuclease. In the preferred embodiment of the present invention, the pertinent DNA sequence is amplified prior to restriction endonuclease digestion.

The amplification may be carried out by synthesizing DNA fragments using a polymerase chain based reaction such as that shown in FIG. 1. Any other method of DNA amplification is suitable for use in the present invention provided it is reasonably accurate and maintains reasonable fidelity of the DNA sequence. Preferably, primers are prepared based on the DNA sequence in the introns surrounding exon 4, the site of the transversion. Preferably the primers are chosen so as to span other CCGG restriction endonuclease sites, as an internal control, so that unique cleavage products result for both the ALA-D[1] and ALA-D[2] allele. For instance sets of DNA primers for the 5' intron having the nucleotide sequence SEQ ID NO: 1 5,'AGACAGACATTAGCTCAGTA3' and for the 3' intron SEQ ID NO: 2 5,'GGCAAAGACCACGTCCATTC3' are preferred.

After amplification, the DNA is digested by the restriction endonuclease recognizing the CCGG DNA sequence. The resultant DNA segments are analyzed for example by electrophoresis on an agarose gel and subsequent fluorographic visualization by staining the DNA with intercalating agents such as ethidium bromide.

Also included in the present invention are any other suitable methods for detecting the polymorphism. Such methods include but are not limited to allele-specific oligonucleotide hybridization, oligonucleotide ligation, ligation amplification and competitive PCR. Conner et al. (1983) Proc. Natl. Acad. Sci. USA, 80:278–282; Saiki et al. (1985) Nature, 324:163–166; Chehab et al. (1987) Nature, 329:293–294; Lungren et al. (1988) Science, 241:1077–1080; Wu et al. (1989) Proc. Natl. Acad. Sci. USA, 86:2757–2760; and Wu et al. (1989) Genomics, 4:560–569.

The present invention also provides a kit for determining a polymorphism in the ALA-D gene comprising a means for extracting DNA from a sample obtained from humans, and means for detecting the presence or absence of ALA-D[2] allele in the DNA sample. In addition, the kit may further comprise a means for amplifying the gene encoding ALA-D or a part thereof.

Also included in the present invention are recombinant DNA molecules encoding ALA-D[1] and ALA-D[2] and any portion of the ALA-D[1] and ALA-D[2] sequence. Thus, the invention includes any sequence of human ALA-D, including the use of primers that involve intronic sequences. For example, ALA-D[1] or ALA-D[2] sequences involving any domains such as the active site, or any part thereof, the zinc binding site, etc. The complete cDNA sequence of human ALA-D[2] is shown in Table 2. The ALA-D[1] sequence differs only by the presence of a G in the third position of codon 59, thereby encoding a lysine residue in position 59 of the ALA-D[1] polypeptide. The invention also includes a recombinant vector containing some or all of the genomic DNA encoding ALA-D[2]. The nucleotide sequence of the genomic DNA containing all coding exons of ALA-D[2] is shown in Table 3. In Table 3, all the coding exons are shown in upper case letters whereas the introns are shown in lower case letter.

The invention further encompasses DNA vectors into which the gene has been cloned and expression systems into which the recombinant vectors have been transferred. Suitable vectors include but are not limited to plasmids, viruses and retroviruses. Suitable expression systems include but are not limited to bacteria, fungi, mammalian cell lines, plant cell lines, insect cell lines and transgenic non-human mammals.

Preferably, the recombinant vectors contain an oligonucleotide having some or all of the sequences as shown in Tables 2 and 3.

TABLE 2

THE COMPLETE cDNA SEQUENCE OF HUMAN ALA-D[2]

| SEQ ID NO: 3 | | | | | | | | | | | | | | |
|---|---|---|---|---|---|---|---|---|---|---|---|---|---|---|
| GAGACCGGAG | | | CGGGAGACAG | | | CGGTGACAGG | | | AGCAGCGGCC | | | GGGAGCCCTT | | 50 |
| AGGGAGGCAG | | | ACAGAGCCTG | | | CAGCCAATGC | | | CCCAGGAGCC | | | CTCGGTTCCA | | 100 |
| ACCAACTGAT | | | GCCCCTGTGC | | | CCACTGCCC | | | ACGCC | ATG | CAG | CCC | CAG | 147 |
| TCC | GTT | CTG | CAC | AGC | GGC | TAC | TTC | CAC | CCA | CTA | CTT | CGG | GCC | 189 |
| TGG | CAG | ACA | GCC | ACC | ACC | ACC | CTC | AAT | GCC | TCC | AAC | CTC | ATC | 231 |
| TAC | CCC | ATC | TTT | GTC | ACG | GAT | GTT | CCT | GAT | GAC | ATA | CAG | CCT | 273 |
| ATC | ACC | AGC | CTC | CCA | GGA | GTG | GCC | AGG | TAT | GGT | GTG | AAC | CGG | 315 |
| CTG | GAA | GAG | ATG | CTG | AGG | CCC | TTG | GTG | GAA | GAG | GGC | CTA | CGC | 357 |
| TGT | GTC | TTG | ATC | TTT | GGC | GTC | CCC | AGC | AGA | GTT | CCC | AAG | GAC | 399 |
| GAG | CGG | GGT | TCC | GCA | GCT | GAC | TCC | GAG | GAG | TCC | CCA | GCT | ATT | 441 |
| GAG | GCA | ATC | CAT | CTG | TTG | AGG | AAG | ACC | TTC | CCC | AAC | CTC | CTG | 483 |
| GTG | GCC | TGT | GAT | GTC | TGC | CTG | TGT | CCC | TAC | ACC | TCC | CAT | GGT | 525 |
| CAC | TGC | GGG | CTC | CTG | AGT | GAA | AAC | GGA | GCA | TTC | CGG | GCT | GAG | 567 |
| GAG | AGC | CGC | CAG | CGG | CTG | GCT | GAG | GTG | GCA | TTG | GCG | TAT | GCC | 609 |
| AAG | GCA | GGA | TGT | CAG | GTG | GTA | GCC | CCG | TCG | GAC | ATG | ATG | GAT | 651 |
| GGA | CGC | GTG | GAA | GCC | ATC | AAA | GAG | GCC | CTG | ATG | GCA | CAT | GGA | 693 |

TABLE 2-continued

THE COMPLETE cDNA SEQUENCE OF HUMAN ALA-D[2]

| | | | | | | | | | | | | | | |
|---|---|---|---|---|---|---|---|---|---|---|---|---|---|---|
| CTT | GGC | AAC | AGG | GTA | TCG | GTG | ATG | AGC | TAC | AGT | GCC | AAA | TTT | 735 |
| GCT | TCC | TGT | TTC | TAT | GGC | CCT | TTC | CGG | GAT | GCA | GCT | AAG | TCA | 777 |
| AGC | CCA | GCT | TTT | GGG | GAC | CGC | CGC | TGC | TAC | CAG | CTG | CCC | CCT | 819 |
| GGA | GCA | CGA | GGC | CTG | GCT | CTC | CGA | GCT | GTG | GAC | CGG | GAT | GTA | 861 |
| CGG | GAA | GGA | GCT | GAC | ATG | CTC | ATG | GTG | AAG | CCG | GGA | ATG | CCC | 813 |
| TAC | CTG | GAC | ATC | GTG | CGG | GAG | GTA | AAG | GAC | AAG | CAC | CCT | GAC | 945 |
| CTC | CCT | CTC | GCC | GTG | TAC | CAC | GTC | TCT | GGA | GAG | TTT | GCC | ATG | 987 |
| CTG | TGG | CAT | GGA | GCC | CAG | GCC | GGG | GCA | TTT | GAT | CTC | AAG | GCT | 1029 |
| GCC | GTA | CTG | GAG | GCC | ATG | ACT | GCC | TTC | CGC | AGA | GCA | GGT | GCT | 1071 |
| GAC | ATC | ATC | ATC | ACC | TAC | TAC | ACA | CCG | CAG | CTG | CTG | CAG | TGG | 1113 |
| CTG | AAG | GAG | GAA | TGA | TGGAGACAGT | | GCCAGGCCCA | | AGAACTAGAA | | | | | 1158 |
| CTTTAAAACG | | | TTCCCGGGGC | | CTCAGACAAG | | TGAAAACCAA | | AGTAAATGCT | | | | | 1208 |
| GCTTTTAGAA | | | CTGT | | | | | | | | | | | |

TABLE 3

THE COMPLETE GENOMIC DNA SEQUENCE OF ALA-D[2]

SEQ ID NO: 4

| | | | | | |
|---|---|---|---|---|---|
| −600 | gagaccatcc | tgggaagcat | ggcaagacct | ccatctctac | aaaaaattcg |
| −550 | aaaattagct | ggatgttgtg | gtgcacacct | gcagtcccag | ctacttggga |
| −500 | ggctgagttg | ggagaaacag | ttgagcccgg | gaggtcaagg | ctgcagtgag |
| −450 | tcgagattgc | accactgcac | tccagcctgg | gcgacagaga | ccctgtgtga |
| −400 | aaaaaaaaaa | aagaagagaa | ttttttttaa | acagtcattg | cttgctcaga |
| −350 | tgtttactttt | aaaagataat | aatgaacaag | aagcagtcac | ataaaataca |
| −300 | agcccaaatt | ttatatcatt | agattctgat | tgtcatgaaa | gtttctaaag |
| −250 | acttactttc | atttctcaac | ttaccttgtt | gaccagcagg | gattggtgaa |
| −200 | ccaggctgtg | agtagcattg | ggctagagag | aggggaggca | ggaatctaga |
| −150 | agagctgttt | tccagatgtg | accatctcct | gaggacaggg | accatgtcct |
| −100 | atgtgccacc | catcacccc | cacagACAGA | GCCTGCAGCC | AATGCCCCAG |
| −50 | GAGCCCTCGG | TTCCAACCAA | CTGATGCCCC | TGTGCCCACT | GGCCCACGCC |
| 1 | ATGCAGCCCC | AGTCCGTTCT | GCACAGCGGC | TACTTCCACC | CACTACTTCCG |
| 51 | GGCCTGGCAG | ACAGCCACCA | CCACCCTCAA | TGCCTCCAAC | CTCATCTACC |
| 101 | CCATCTTTGT | CACgtgagtc | tccaagaatg | ggccaggcct | ctgctctgct |
| 151 | ggttggggtt | ggggttgggg | agggagtgtt | gactggagcg | ggcatcagta |
| 201 | tggctggggg | tggcaaagtg | agctgtcagc | ttgaaattca | aggcactgga |
| 251 | agcaggctac | ttggattaag | gacaggaatc | ttaggaacaa | aacaaactttt |
| 301 | gaaagaactc | attcatccca | ttttggaaaat | tagaagaata | acccttgcct |
| 351 | gccatctga | gctcttgcag | taagacagaa | gctgagaagg | tgctctgtac |
| 401 | attgtaaagt | gctatgtacc | tgtaagagat | ggcagtcatt | gaggctgggc |
| 451 | acggtggctc | acgcctgtaa | tcccagcact | ttgggaggct | gaggcaggcg |
| 501 | gatcacgagg | tcaggagatc | gagaccatcc | tggctaatat | ggtgaaaccc |
| 551 | tgtctctact | aaaaacacaa | agaaattagc | caggcgtggt | ggcgggtgcc |
| 601 | tgtagtccca | gctacttggg | aggctgaggc | aggagaatgg | cgtgaacccg |
| 651 | ggaggcggag | cttgcagtga | gccgagattg | caccacttca | ctccagcctg |
| 701 | ggcgacagag | ccagactcca | tctcaaaaaa | aaaaaaaaaa | aaaagagatg |
| 751 | gcaatcgtga | ttgttaataa | taatgcagac | atttactgag | tacttactat |
| 801 | ctaccaggta | ctatgctaag | cacctacaca | cattatctca | ttcaattctg |
| 851 | agagcatttg | tatgaagaag | gagtagctat | cctctagaac | atcagctcca |
| 901 | tgagggcagg | gatgtttgtc | tattttgttc | actgttgtat | catcagggcc |
| 951 | tagaacagta | cttggcacat | aataagtact | caataaatat | ttgttgaatg |
| 1001 | aatgaattaa | ccacgcatga | tatagatgaa | ggcctaaggc | tcaaagagat |
| 1051 | gatagaactt | ggccacggtc | acccaggcag | taagtggctg | ggatagaaag |
| 1101 | caaggacctg | ccaaattcag | agtccaagtt | cttaaccact | taattccttc |
| 1151 | ctgtaattac | cgttcttta | gtacagttgc | tagtgttgtc | actgttattc |
| 1201 | ttgttgttcc | tattattatt | tcaggccctg | ggcttggcca | ggcagggaag |
| 1251 | ccagacactg | gatcccatcc | tcctcccacc | atctccactt | ccatatttct |
| 1301 | ttcctgcttc | ccaaccatcc | ctctcagtcg | cccccgcacc | actggccctt |
| 1351 | cccacagcta | ccaatccata | tcccacccc | gctcttgcag | GGATGTTCCT |
| 1401 | GATGACATAC | AGCCTATCAC | CAGCCTCCCA | GGAGTGGCCA | Ggtaggagac |
| 1451 | gtgggagttgg | ggggccagcg | ggtggtggag | ggagagattc | cacaggtgga |
| 1501 | agtgctggga | ggcagaagca | gacctaggaa | gtagaagatg | cggacagaca |
| 1551 | gacattagct | cagtagagga | aagggtttcc | ccggggccag | agctgttcca |
| 1601 | cagtggaagg | ggcagcccca | taaagtaaag | agctacccat | cacccgagac |
| 1651 | gtcgtggcag | aggctgttgc | agaagggagc | tgaactgcag | atgggagttc |
| 1701 | aaaaagaggg | cctcgaagga | gccttccaca | gccgaattcc | ggagctctgc |
| 1751 | tactcagggc | ctcagtcttc | cctcctattt | agtggatgca | tccctgcccc |
| 1801 | ttctgtcctg | ggggcttgag | ccctcctggt | gccatatgca | gcttggttttc |
| 1851 | taacagaggc | acacagtgtg | gtggggtccg | gaggaccgtt | gcctgggacc |
| 1901 | tgccttccttt | caaccctct | acccacaccc | acacagGTAC | GGTGTGAACC |
| 1951 | GGCTGGAAGA | GATGCTGAGG | CCCTTGGTGG | AAGAGGGCCT | ACGCTGTCTC |
| 2001 | TTGATCTTTG | GCGTCCCCAG | CAGAGTTCCC | AAGgtgaaga | atcaaaggaa |
| 2051 | gggctaagaa | gggaggttgc | ctcacgcccg | taatcccagc | actttgggag |
| 2101 | gccaaagtgg | gtggatcact | tgagcccagg | attttgagac | cagcctggac |

TABLE 3-continued

THE COMPLETE GENOMIC DNA SEQUENCE OF ALA-D[2]

| | | | | |
|---|---|---|---|---|
| 2151 aacatggcaa | aacccatctc | tacaaaaaat | acaaaagtta | gctgggtgtg |
| 2201 ggggtatgtg | cctgtagtcc | cagctactcg | ggaggtggag | aggtgggagg |
| 2251 attgcttgag | cccagaaagt | cgaggctgca | gtgagccaaa | atcgcgccag |
| 2301 tgcactctag | cctgggtgac | agagcaagac | cctgtctcca | atacaaacag |
| 2351 aaaaaggaag | ggaggttggg | caaaggtgga | ctgagggtcc | acactgactg |
| 2401 caccctcact | cccacattgt | gctggccctg | gggccacagg | tgaatggacg |
| 2451 tggtctttgc | ccttaagtca | gcacccatgt | agggtcggtc | ctctgtgctt |
| 2501 cctatccag | gggctgtgat | gatgaaggaa | ggagaaggcc | agggctatgc |
| 2551 tctgtgatgg | ctgtcatcct | gccttccaaa | gctacatgta | atagacacac |
| 2601 tgctttgtcc | ctcccctgcc | cctagGACGA | GCGGGGTTCC | GCAGCTGACT |
| 2651 CCGAGGAGTC | CCCAGCTATT | GAGGCAATCC | ATCTGTTGAG | GAAGACCTTC |
| 2701 CCCAACCTCC | TGGTGGCCTG | TGATGTCTGC | CTGTGTCCCT | ACACCTCCCA |
| 2751 TGGTCACTGC | Ggtgagttcc | ctccctccca | ccagccctgc | tgccacccac |
| 2801 actcctactg | cccacttctc | aacagggtgg | ggacagccag | ggcccaaggt |
| 2851 gctccccaaa | acccagtcat | ctgtcctgaa | gGGCTCCTGA | GTGAAAACGG |
| 2901 AGCATTCCGG | GCTGAGGAGA | GCCGCCAGCG | GCTGGCTGAG | GTGGCATTGG |
| 2951 CGTATGCCAA | GGCAGgtgag | tgaaccacca | gcagggatgg | gcacctctgg |
| 3000 gtcahhaggt | ggcagagtgg | ctaggagggc | cccagagttc | tgaaggccac |
| 3051 cctctgcccc | ccagGATGTC | AGGTGGTAGC | CCCGTCGGAC | ATGATGGATG |
| 3101 GACGCGTGGA | AGCCATCAAA | GAGGCCCTGA | TGGCACATGG | ACTTGGCAAC |
| 3151 AGGgtaaggg | cagggaatgc | agcacagggc | tggcaggaga | tagtctgcac |
| 3201 cagccctgcc | cccgtgtctg | ctaagaatca | cagaactgcc | gggcgtgttg |
| 3251 gctcacacct | gtagtcccag | cactttggga | ggctgaggca | ggtagatcac |
| 3301 ttgaggtcag | gggttcaaga | ccagcctggc | caacatggtg | aaaccccatc |
| 3351 tctactaaaa | acacaaaaat | tagctgggcg | tggtggcagg | cgcctgcaat |
| 3401 cccagctact | ggggaggctg | aggcaggaga | atcgcttgaa | cccacgaggc |
| 3451 agtgagctga | gatcatgcca | ctgcacttca | gcctggatga | cagagctaga |
| 3501 ctccatctca | aaaaaaaaaa | gaatcacaga | actgaagaca | gtgctggatg |
| 3551 aggcttggg | gaaccattta | aacctctggg | cctctgcagg | gaaatcaagc |
| 3601 ccagcactcc | aacaggacca | gaacacaggc | agtctccttc | ccagcctagg |
| 3651 ttctttctct | ccctgccaca | tcaccctggg | atacctggca | agggccgaat |
| 3701 aagccaagac | ctccattgtc | tccccatagG | TATCGGTGAT | GAGCTACAGT |
| 3751 GCCAAATTTG | CTTCCTGTTT | CTATGGCCCT | TTCCGgtgag | caggggtggg |
| 3801 caggggtctg | ctgtgaatcc | ctgcccttg | gcccaaagct | ggagcccacc |
| 3851 ctgatgactc | tgctttgcag | GGATGCAGCT | AAGTCAAGCC | CAGCTTTTGG |
| 3901 GGACCGCCGC | TGCTACCAGC | TGCCCCCTGG | AGCACGAGGC | CTGGCTCTCC |
| 3951 GAGCTGTGgt | gagtgactag | gacttgagcc | ccaccctcag | cccctccta |
| 4001 ggcaccaccc | acattatacc | ctcatcccctt | agGACCGGGA | TGTACGGGAA |
| 4051 GGAGCTGACA | TGCTCATGGT | GAAGCCGGGA | ATGCCCTACC | TGGACATCGT |
| 4101 GCGGGAGGTA | AAGGACAAGg | tgagcacagg | tacgaggcaa | aggggctca |
| 4151 gggggctggg | acagagtttt | ccacagactc | tggaatctca | gagttggaag |
| 4201 cagtttgccc | ttaagcatgc | atcctctcct | cccccttcct | gcccaggaac |
| 4251 catcgtggcc | ttctatgtcg | gggcttgcac | gagcctcaaa | cagccctgct |
| 4301 ttaacagttc | aagagtgggc | caggctgcca | gccgcagtaa | cccaggacac |
| 4351 ggggctcaag | atggtcacag | attgagcagg | ggggaaggga | cgcttccaga |
| 4401 gccacatcca | ccctccattt | cagcctgtct | ccctgtctgc | ttccctgcag |
| 4451 CACCCTGACC | TCCCTCTCGC | CGTGTACCAC | GTCTCTGGAG | AGTTTGCCAT |
| 4501 GCTGTGGCAT | GGAGCCCAGG | CCGGGGCATT | TGATCTCAAG | GCTGCCGTAC |
| 4551 TGGAGGCCAT | GACTGCCTTC | CGCAGAGCAG | gtaggcaggc | aagggtgggg |
| 4601 tgttttgacc | tgcgccacag | ggactgataa | gcactctgcc | tagatcgggg |
| 4651 aacgacgtcc | tgagagcttg | ggatcttatt | ccgggaatta | ctagtgatct |
| 4701 aaacagacac | acactgagga | agagatatgg | aactgcagca | tagaacacgg |
| 4751 cccggtgaag | caagcagagc | ccttcatttt | tggttgtgag | aacgtggcaa |
| 4801 gccacttctc | tgaacctcag | tgtcctcacc | cataactgga | taactgggga |
| 4851 taagatacct | ggtgcgtggt | tgtcctgagg | attaaatgaa | gtaatatcac |
| 4901 tccataaagg | ggactcattt | tgttagaatt | gcacaccagc | atgggaagga |
| 4951 acttgcctct | tatatttcct | tcactgtgca | ttttattctt | tggtaaactg |
| 5001 aggccccaaa | agaggaaatg | acttgcccaa | gaaatagagt | ttcccaaagc |
| 5051 tgggctccgt | ctcatgtggt | gtgcccacag | gctgtgcttc | ttcatggtag |
| 5101 ccttcttccc | cgcctgcct | tcccatcgca | gaaggtgtgc | tcagagctga |
| 5151 tcagcgtccc | cccagcaact | ttctgcatct | ctcccaacac | agGTGCTGAC |
| 5201 ATCATCATCA | CCTACTACAC | ACCGCAGCTG | CTGCAGTGGC | TGAAGGAGGA |
| 5251 ATGATGGAGA | CAGTGCCAGG | CCCAAGAACT | AGAACTTTAA | AACGTTCCCG |
| 5301 GGGCCTCAGA | CAAGTGAAAA | CCAAAGTAAA | TGCTGCTTTT | AGAACTGTgc |
| 5351 cctcatgccc | tcttcctgct | cacatgctag | cggggcccag | cagccctggg |
| 5401 tggttttgcc | agcatgctaa | ctcttgtaac | tcgcagctgc | atcctatgag |
| 5451 ctctcccaag | ctt | | | |

Methods of cloning genes in the proper orientation and with the proper flanking sequences, transforming the genes into a suitable host cell and expressing and purifying the proteins are known in the art and examples are provided below. Detailed DNA cloning methods are provided in a variety of sources. See e.g. Sambrook et al., Molecular Cloning A Laboratory Manual, Cold Spring Harbor Laboratory Press, New York, (1989).

Gene transfer into an expression system can be accomplished by any of the well known means in the art. For example, methods of gene transfer include but are not limited to $CaCl_2$ mediated transfection and electroporation in the case of bacteria, and in the case of eukaryotic cells, CaPO$_4$ mediated transfection, viral infection including retroviral latent infection, electroporation, liposome mediated DNA transfer and microinjection among others.

A transgenic non-human mammal, for instance a mouse, carrying either the human ALA-D$^1$ or ALA-D$^2$ allele can be used as a model system to determine and compare the contribution of the ALA-D polymorphism to the pathophysiology of lead poisoning, for example, extent of lead uptake, tissue-specific distribution of lead, and tissue-specific inhibition of ALA-D by lead.

In an embodiment of this invention a transgenic mammal in which a substantial portion of its germ and somatic cells contain a recombinant activated human ALA-D$^1$ or ALA-D$^2$ sequence can be produced as follows.

For the purposes of gene transfer experiments, the complete ALA-D$^1$ and ALA-D$^2$ genomic sequence including 2.1 kilobase pair (kb) of 5' untranslated sequence should be used. C57BL/6 mice, whose haploid genome contains only one copy of the mouse ALA-D gene, can be used as sources of eggs and sperm for in vitro fertilization, as described by Gordon et al. (1983) Methods Enzymol. 101:411–432 although any suitable method of making transgenic animals is acceptable. Briefly, the 10–14 week old females are superovulated by intraperitoneal injection of 5 I.U. of pregnant mare's serum followed 48 hours later by 2.5 I.U. of human chorionic gonadotropin. These mice are then sacrificed and the eggs removed. The 10–14 week old males are also sacrificed and the mature sperm harvested from the vas deferens and caudal epididymis. The eggs and sperm are frozen prior to in vitro fertilization. To increase fertilization, zona drilling of each egg is performed using micropuncture techniques. Following in vitro fertilization, the zygotes with prominent pronuclei are selected and loaded into culture dishes containing microdrops of culture medium under mineral oil. Next, the embryos are placed on the stage of a phase contrast microscope and, while being held in place by a suction needle, the human ALA-D genomic DNA is microinjected until swelling of the pronuclei is noticeable.

After microinjection of about 100–200 copies of one of the ALA-D alleles, the embryos are returned to the incubator and examined after 1 hour. Survivors are selected and implanted into the oviducts of pseudopregnant females obtained by mating with vasectomized males. After the pups are born, tail clips are used as a source of DNA for Southern hybridization (or PCR amplification) with a unique portion of the first human ALA-D intron which has no homology with the mouse intron. Positive animals are used for breeding. Second generation animals carrying the human ALA-D allele must carry the gene in the germ line.

EXAMPLE 1

Screening for ALA-D polymorphisms

In order to screen for the ALA-D restriction fragment length polymorphisms (RFLP), an 1170 base pair (bp) cDNA isolated from an adult liver cDNA library according to the method described by Wetmur et al., "Human Delta-aminolevulinate Dehydratase: Nucleotide Sequence of a Full-length cDNA Clone", Proc. Natl. Acad. Sci. USA, 83:7703–7707 (1986), was used as a probe for restriction endonuclease analysis of human lymphoblastoid cell genomic DNA isolated as described in Sambrook et al. (1989) and analyzed using the electrophoresis, transfer and hybridization methods of Southern, "Detection of Specific Sequences Among DNA Fragments Separated by Gel Electrophoresis", J. Mol. Biol., 98:503–517 (1975). DNA was obtained from over 30 unrelated individuals, digested with more than 20 restriction endonucleases and fragments greater than 1 kb were analyzed by Southern blot analysis.

No polymorphism was detected by Southern blot hybridization using a battery of restriction endonucleases with six base recognition sequences. One polymorphism was detected using restriction endonucleases with four base recognition sequences. With RsaI, the presence or absence of the polymorphic site resulted in 2.2 or 3.0 kb fragments respectively.

Based on the distribution of Rsa I sites in the ALA-D gene, the RsaI polymorphism was located in Exon 4 (the third coding exon in Table 3), 3.4 kb 5' of the polyadenylation signal and 2.0 kb 3' of the initiation codon. The polymorphism is a single base pair change from T to C at nucleotide 168 of the cDNA coding sequence. This transition does not affect the amino acid sequence of ALA-D.

EXAMPLE 2

Cloning the ALA-D$^2$ gene

In order to clone the ALA-D$^2$ gene a cDNA sequence encoding ALA-D$^2$ was obtained by the following method. RNA was extracted from lymphoblastoid cells of an individual who had been shown to be homozygous for the ALA-D$^2$ allele by starch gel electrophoresis. The method of Chirgwin et al., (1979) "Isolation of Biologically Active Ribonucleic Acid From Sources Enriched in Ribonuclease", Biochem., 18:5294–5299 was used with the following modifications: the guanidinium thiocyanate solution contained 25 mM sodium thiocyanate and 0.03% instead of 0.1% Antifoam A; the CsCl solution contained 0.02% instead of 0.2% diethylpyrocarbonate. cDNA synthesis was carried out using the cDNA Synthesis System of BRL, Inc. according to the manufacturer's instructions. Briefly, 10 mg of total RNA was reverse transcribed into cDNA using oligo-dT as the primer. All oligodeoxynucleotides were synthesized on an Applied Biosystems Model 380B oligonucleotide synthesizer using standard phosphoramidite chemistry according to the manufacturer's instructions. ALA-D-specific primers for the 5' and 3' untranslated regions of the gene SEQ ID NO: 5 5'AGAGGCGAATTCCCAATGC-CCCAGGAGCCC3' and

SEQ ID NO: 6 5'GTTCTAAAGCTTGGGCCTG-GCACTGTCTCC3' respectively) were synthesized to include 5' EcoRI or HindIII sites, respectively. Amplification of ALA-D cDNA was carried out using the polymerase chain reaction (PCR) according to the method of Saiki et al. (1988) "Primer-directed Enzymatic Amplification of DNA With a Thermostable DNA Polymerase", Science, 239:487–491. Ten to 12.5 µl of first strand mixture, without prior precipitation, was mixed with ALA-D-specific primers. The cDNA-RNA hybrid was denatured by heating at 100° C. for 5 minutes, then quenching on ice for 5 minutes. 45 cycles of amplification were executed using denaturation at 94° C. for 1 minute, annealing at 53° C. for 1 minute and extension at 72° C. for 3 minutes with the final cycle extended to 10 minutes. PCR was performed using either the GeneAmp DNA Amplification Reagent Kit according to the manufacturer's instructions (Perkin-Elmer Cetus) or using Taq DNA Polymerase according to the manufacturer's instructions (Promega) with 1.0 to 2.2 µM primers and 20 µg/ml genomic DNA or 4 ng/ml plasmid DNA template.

Following the appropriate methods of Sambrook et al. (1989), the cDNA PCR product was extracted once with phenol:chloroform:isoamyl alcohol (25:24:1), twice with chloroform:isoamyl alcohol (24:1), ethanol precipitated, and digested with EcoRI and HindIII. The digest was heated to 65° C. for 20 minutes, ethanol precipitated, redissolved, ligated into EcoRI and HindIII digested pUC19 (25 µg/ml) and transformed into *E. Coli* DH5 using the protocol of Kushner, "Genetic Engineering, Boyer, Nicosia, eds. Elsevier/North-Holland Biomedical Press, Amsterdam, pp. 17–23 (1978) without dimethylsulfoxide. Colonies not expressing β-galactosidase were propagated, and plasmid DNAs were prepared. T4 DNA ligase, T4 polynucleotide kinase and all restriction endonucleases were purchased from New England Biolabs, Inc. or Promega, Inc. and used according to the manufacturer's instructions.

Double-stranded DNA sequencing of supercoiled plasmid templates was performed according to the instructions in the Sequenase DNA Sequencing Kit of United States Biochemical Corporation, Inc., at least 2 µg of DNA was used in each reaction. The cDNA sequence obtained is presented in Table 2.

The ALA-D$^2$ cDNA sequence obtained showed that a single base pair change of a G to C at position 177 compared to the ALA-D$^1$ sequence. Wetmur et al. (1986). The transversion results in a change of amino acid 59 from positively charged lysine to neutral asparagine and in the creation of an MspI (CCGG) restriction endonuclease site. In the genomic DNA, the MspI polymorphism is located in exon 4 (the third coding exon in Table 3), only 9 base pairs away from the RsaI polymorphic site described in Example 1. As a result, the same PCR method as described in example 3 can be used to amplify DNA for the determination of the RsaI polymorphism and the presence or absence of the MspI restriction endonuclease site.

The only nucleotide sequence difference found between the sequences of the ALA-D$^1$ and ALA-D$^2$ alleles corresponds to a change in one predicted amino acid from a positive lysine to a neutral asparagine, which accounts for the difference in the electrophoretic mobilities of the ALA-D 1-1, ALA-D 1-2 and ALA-D 2-2 charge isozymes.

EXAMPLE 3

Correlation of ALA-D genotype and ALA-D charge isozyme phenotype

In order to correlate ALA-D genotype and charge isozyme phenotype, aliquots of residual blood collected with informed consent from patients &&&KEPundergoing Tay-Sachs screening at Mount Sinai and Beth Israel Hospitals in New York City were used for either gel electrophoresis or PCR analysis, or both. Blood samples for analysis by electrophoresis were centrifuged at 1600 rpm in a Sorvall RT6000 for 30 minutes and the plasma and buffy coat were removed. The remaining red blood cells were mixed several times by inverting with one half volume of saline and centrifuged at 1600 rpm for 10 minutes. This erythrocyte washing procedure was repeated. A 0.5 ml sample of packed erythrocytes was mixed with an equal volume of lysis buffer (1 mM $KH_2PO_4$+KOH, pH 6.8, 1 mM $MgCl_2$, 1 mM dithiothreitol (DTT) and 0.05% Triton X-100) and centrifuged for 1 minute at 12,000 rpm in a Fisher Model 235C microcentrifuge. Lysed red blood cell samples were frozen until used.

The ALA-D isozyme phenotypes were determined following cellulose acetate gel electrophoresis (Cellogel). Lysates (7.5 ml) were diluted into 0.01M phosphate buffer, applied to the gel and separated by electrophoresis for 2 hr at 200 V at 4° C. in 0.1M sodium phosphate, pH 6.8. The cellogel was first incubated in PBS with rabbit polyclonal anti-human ALA-D antibody directed at human ALA-D purified by the method of Anderson and Desnick, "Purification and Properties of delta-aminolevulinate Dehydratase from Human Erythrocytes", J. Biol. Chem., 254:6924–6930 (1979), then with biotinylated goat anti-rabbit IgG and finally with a preformed avidin and biotinylated horseradish peroxidase complex as described in the Vectastain ABC kit (Vector Laboratories).

In order to determine the ALA-D genotype, samples for PCR analysis were prepared by the whole blood protocol as described by Perkin-Elmer, Cetus. Oligodeoxynucleotides were synthesized 5' and 3' to the exon with the ALA-D polymorphisms. The 5' and 3' oligodeoxynucleotide sequences were SEQ ID NO: 1 5'AGACAGACATTAGCTCAGTA3' and
SEQ ID NO: 2 5'GGCAAAGACCACGTCCATTC3' respectively. The amplification program was the same as described in Example 2 except the annealing temperature was 55° C.

PCR products were cleaved with RsaI and/or MspI and analyzed by fluorography following agarose gel electrophoresis with ethidium bromide. The 916 bp PCR product was unaffected by RsaI digestion if the allele was RsaI$^-$, but was cleaved into 523 and 393 bp fragments if the allele was RsaI$^+$. The Bluescript SK (Stratagene, Inc.) vector, which contains two RsaI cleavage sites, was added to RsaI-only digestion reactions as a control for incomplete digestion.

All blood samples that were determined to be either ALA-D 1-2 or ALA-D 2-2 and eighty seven blood samples that were determined to be ALA-D 1-1 by cellulose acetate gel analysis were further analyzed for ALA-D$^1$ and ALA-D$^2$ alleles by MspI cleavage of the PCR products. The 916 bp PCR product was cleaved by MspI digestion into a 582 bp fragment if the allele was ALA-D$^1$ and into a 511 bp fragment if the allele was ALA-D$^2$. The products were analyzed by agarose gel electrophoresis. In all cases of ALA-D 1-2 individuals the expected heterozygote agarose gel pattern was observed. Likewise, MspI cleavage of PCR products from all samples with the ALA-D 2-2 phenotype resulted in a single 511 bp band. Haplotype assignments of RsaI and MspI heterozygotes were made by double-digestion.

Analysis of a random population of 428 normal Caucasian individuals revealed that the ALAD$^1$(MspI$^{31}$) and ALAD$^2$ (MspI$^+$) allele frequencies were 0.88 and 0.12, respectively. The allele frequencies for the RsaI$^-$ and RsaI$^+$ alleles in the same population were 0.75 and 0.25, respectively. Individually, the MspI and RsaI RFLPs were in Hardy-Weinberg equilibrium ($\chi^2$MspI=3.5, df=2, p>0.10; $\chi^2$RsaI= 1.88, df=2, p>0.25). Based on the above frequencies, the expected MspI/RsaI haplotypes would be ALAD$^1$ (MspI$^-$)/RsaI$^+$, 0.66; ALAD$^1$/RsaI$^+$, 0.22; ALAD$^2$/RsaI$^{31}$, 0.09 and ALAD$^2$/RsaI$^+$, 0.03. However, the two RFLPs were in linkage disequilibrium ($\chi^2$=22, df=1, p<0.001). Of the 259 ALAD$^1$ alleles studied, 27.4% were RsaI$^+$, whereas only 5% of 101 ALAD$^2$ alleles were RsaI+. The expected number of ALAD$^1$/RsaI+ and ALAD$^2$/RsaI+ were each 25%, thus the ALAD$^2$/RsaI+ allele was highly underrepresented.

The polymorphism information content (PIC) for these haplotypes is 0.45, a reasonably informative (0.5 >PIC>0.25) value. Botstein et al., (1980) "Construction and Genetic Linkage Map in Man Using Restriction Fragment Length Polymorphism", Am. J. Hum. Genet., 32:314–31.

Of the samples where ALA-D electrophoretic phenotypes were determined by Cellogel electrophoresis and MspI genotypes all were determined by RFLP analysis, all phenotypes correlated with genotypes. In another unrelated study, one individual was identified by starch gel electrophoresis as having the ALA-D 2-2 isozyme phenotype, but genotype analysis revealed that this individual had one ALA-D² allele and one ALA-D¹ allele. Thus, there may be another (other) rare mutation(s) which lead to the same charge isozyme phenotype or, alternatively, this ALA-D¹ allele which does not have the MspI site may not have been expressed. Nevertheless, the observed nucleotide substitution results in both the MspI RFLP and the polymorphic ALA-D charge isozymes in the vast majority of individuals.

We claim:

1. A method for detecting polymorphism in a gene encoding δ-aminolevulinate dehydratase in a subject comprising said gene comprising the steps of obtaining a biological sample from the subject and analyzing the sample for the presence of a gene encoding δ-aminolevulinate dehydratase having the following sequence

TABLE 3

| SEQ ID NO: 4 | | | |
|---|---|---|---|
| −600 | gagaccatcc | tgggaagcat | ggcaagacct |
| | | ccatctctac | aaaaaattcg |
| −550 | aaaattagct | ggatgttgtg | gtgcacacct |
| | | gcagtcccag | ctacttggga |
| −500 | ggctgagttg | ggagaaacag | ttgagcccgg |
| | | gaggtcaagg | ctgcagtgag |

TABLE 3-continued

| | | | |
|---|---|---|---|
| -450 | tcgagattgc | accactgcac | tccagcctgg |
| | | gcgacagaga | ccctgtgtga |
| -400 | aaaaaaaaaa | aagaagagaa | tttttttaa |
| | | acagtcattg | cttgctcaga |
| -350 | tgtttactt | aaaagataat | aatgaacaag |
| | | aagcagtcac | ataaaataca |
| -300 | agcccaaatt | ttatatcatt | agattctgat |
| | | tgtcatgaaa | gtttctaaag |
| -250 | acttacttc | atttctcaac | ttaccttgtt |
| | | gaccagcagg | gattggtgaa |
| -200 | ccaggctgtg | agtagcattg | ggctagagag |
| | | aggggaggca | ggaatctaga |
| -150 | agagctgttt | tccagatgtg | accatctcct |
| | | gaggacaggg | accatgtcct |
| -100 | atgtgccacc | catcacccc | cacagACAGA |
| | | GCCTGCAGCC | AATGCCCCAG |
| -50 | GAGCCCTCGG | TTCCAACCAA | CTGATGCCCC |
| | | TGTGCCCACT | GGCCCACGCC |
| 1 | ATGCAGCCCC | AGTCCGTTCT | GCACAGCGGC |
| | | TACTTCCACC | CACTACTTCCG |
| 51 | GGCCTGGCAG | ACAGCCACCA | CCACCCTCAA |
| | | TGCCTCCAAC | CTCATCTACC |
| 101 | CCATCTTTGT | CACgtgagtc | tccaagaatg |
| | | ggccaggcct | ctgctctgct |
| 151 | ggttggggtt | ggggttgggg | agggagtgtt |
| | | gactggagcg | ggcatcagta |
| 201 | tggctggggg | tggcaaagtg | agctgtcagc |
| | | ttgaaattca | aggcactgga |
| 251 | agcaggctac | ttggattaag | gacaggaatc |
| | | ttaggaacaa | aacaaacttt |
| 301 | gaaagaactc | attcatccca | tttggaaaat |
| | | tagaagaata | accctgcct |
| 351 | gccatcctga | gctcttgcag | taagacagaa |
| | | gctgagaagg | tgctctgtac |
| 401 | attgtaaagt | gctatgtacc | tgtaagagat |
| | | ggcagtcatt | gaggctgggc |
| 451 | acggtggctc | acgcctgtaa | tcccagcact |
| | | ttgggaggct | gaggcaggcg |
| 501 | gatcacgagg | tcaggagatc | gagaccatcc |
| | | tggctaatat | ggtgaaaccc |
| 551 | tgtctctact | aaaaacacaa | agaaattagc |
| | | caggcgtggt | ggcgggtgcc |
| 601 | tgtagtccca | gctacttggg | aggctgaggc |
| | | aggagaatgg | cgtgaacccg |
| 651 | ggaggcggag | cttgcagtga | gccgagattg |
| | | caccacttca | ctccagcctg |
| 701 | ggcgacagag | ccagactcca | tctcaaaaaa |
| | | aaaaaaaaaa | aaaagagatg |
| 751 | gcaatcgtga | ttgttaataa | taatgcagac |
| | | atttactgag | tacttactat |
| 801 | ctaccaggta | ctatgctaag | cacctacaca |
| | | cattatctca | ttcaattctg |
| 851 | agagcatttg | tatgaagaag | gagtagctat |
| | | cctctagaac | atcagctcca |
| 901 | tgagggcagg | gatgtttgtc | tattttgttc |
| | | actgttgtat | catcagggcc |
| 951 | tagaacagta | cttggcacat | aataagtact |
| | | caataaatat | ttgttgaatg |
| 1001 | aatgaattaa | ccacgcatga | tatagatgaa |
| | | ggcctaaggc | tcaaagagat |
| 1051 | gatagaactt | ggccacggtc | acccaggcag |
| | | taagtgctg | ggatagaaag |
| 1101 | caaggacctg | ccaaattcag | agtccaagtt |
| | | cttaaccact | taattccttc |
| 1151 | ctgtaattac | cgttcttta | gtacagttgc |
| | | tagtgttgtc | actgttattc |
| 1201 | ttgttgttcc | tattattatt | tcaggccctg |
| | | ggcttggcca | ggcagggaag |
| 1251 | ccagacactg | gatcccatcc | tcctcccacc |
| | | atccactt | ccatatttct |
| 1301 | ttcctgcttc | ccaaccatcc | ctctcagtcg |
| | | cccccgcacc | actggcctt |
| 1351 | cccacagcta | ccaatccata | tcccaccccc |
| | | gctcttgcag | GGATGTTCCT |
| 1401 | GATGACATAC | AGCCTATCAC | CAGCCTCCCA |
| | | GGAGTGGCCA | Ggtaggagac |
| 1451 | gtggagttgg | ggggccagcg | ggtggtggag |
| | | ggagagattc | cacaggtgga |
| 1501 | agtgctggga | ggcagaagca | gacctaggaa |
| 1551 | gacattagct | gtagaagatg | cggacagaca |
| | | cagtgagga | aagggtttcc |
| 1601 | cagtggaagg | ccggggccag | agctgttcca |
| | | ggcagcccca | taaagtaaag |
| 1651 | gtcgtggcag | agctaccat | cacccgagac |
| | | aggctgttgc | agaagggagc |
| 1701 | aaaaagaggg | tgaactgcag | atgggagttc |
| | | cctcgaagga | gccttccaca |
| 1751 | tactcagggc | gccgaattcc | ggagctctgc |
| | | ctcagtcttc | cctcctattt |
| 1801 | ttctgtcctg | agtggatgca | tccctgcccc |
| | | ggggcttgag | ccctcctggt |
| 1851 | taacagaggc | gccatatgca | gcttggtttc |
| | | acacagtgtg | gtggggtccg |
| 1901 | tgccttcctt | gaggaccgtt | gcctgggacc |
| | | caaccctct | accacacacc |
| 1951 | GGCTGGAAGA | acacagGTAC | GGTGTGAACC |
| | | GATGCTGAGG | CCCTTGGTGG |
| 2001 | TTGATCTTTG | AAGAGGGCCT | ACGCTGTCTC |
| | | CGTCCCAG | CAGAGTTCCC |
| 2051 | gggctaagaa | AAGgtgaaga | atcaaaggaa |
| | | gggaggtgc | ctcacgcccg |
| 2101 | gccaaagtgg | taatcccagc | actttgggag |
| | | | tgagcccagg |
| 2151 | aacatggcaa | gtggatcact | cagctggac |
| | | attttgagac | tacaaaaaat |
| 2201 | ggggtatgtg | aacccatctc | gctgggtgtg |
| | | acaaaagtta | cagctactcg |
| 2251 | attgcttgag | cctgtagtcc | aggtgggagg |
| | | ggaggtggag | cgaggctgca |
| 2301 | tgcactctag | cccagaaagt | atcgcgccag |
| | | gtgagccaaa | agagcaagac |
| 2351 | aaaaaggaag | cctgggtgac | atacaaacag |
| | | cctgtctcca | ggaggtggga | caaaggtgga |
| | | | ctgaggggtcc | acactgactg |
| 2401 | caccctcact | cccacattgt | gctggccctg |
| | | gggccacagg | tgaatggacg |
| 2451 | tggtctttgc | ccttaagtca | gcacccatgt |
| | | agggtcggtc | ctctgtgctt |
| 2501 | ccttatccag | gggctgtgat | gatgaaggaa |
| | | ggagaaggcc | agggctatgc |
| 2551 | tctgtgatgg | ctgtcatcct | gccttccaaa |
| | | gctacatgta | atagacacac |
| 2601 | tgcttttgtcc | ctcccctgcc | cctagGACGA |
| | | GCGGGGTTCC | GCAGCTGACT |
| 2651 | CCGAGGAGTC | CCCAGCTATT | GAGGCAATCC |
| | | ATCTGTTGAG | GAAGACCTTC |
| 2701 | CCCAACCTCC | TGGTGGCCTG | TGATGTCTGC |
| | | CTGTGTCCCT | ACACCTCCCA |
| 2751 | TGGTCACTGC | Ggtgagttcc | ctccctccca |
| | | ccagccctgc | tgccacccac |
| 2801 | actcctactg | cccacttctc | aacaggtgg |
| | | ggacagccag | ggcccaaggt |
| 2851 | gctccccaaa | acccagtcat | ctgtcctgaa |
| | | gGGCTCCTGA | GTGAAAACGG |
| 2901 | AGCATTCCGG | GCTGAGGAGA | GCCGCCAGCG |
| | | GCTGGCTGAG | GTGGCATTGG |
| 2951 | CGTATGCCAA | GGCAGgtgag | tgaaccacca |
| | | gcagggatgg | gcacctctgg |
| 3000 | gtcahhaggt | ggcagagtgg | ctaggagggc |
| | | cccagagttc | tgaaggccac |
| 3051 | cctctgcccc | ccagGATGTC | AGGTGGTAGC |
| | | CCCGTCGGAC | ATGATGGATG |
| 3101 | GACGCGTGGA | AGCCATCAAA | GAGGCCCTGA |
| | | TGGCACATGG | ACTTGGCAAC |
| 3151 | AGGgtaaggg | cagggaatgc | agcacagggc |
| | | tggcaggaga | tagtctgcac |
| 3201 | cagccctgcc | cccgtgtctg | ctaagaatca |
| | | cagaactgcc | gggcgtgttg |
| 3251 | gctcacacct | gtagtcccag | cactttggga |
| | | ggctgaggca | ggtagatcac |
| 3301 | ttgaggtcag | gggttcaaga | ccagcctggc |
| | | caacatgtg | aaaccccatc |
| 3351 | tctactaaaa | acacaaaaat | tagctgggcg |
| | | tggtggcagg | cgcctgcaat |
| 3401 | cccagctact | ggggaggctg | aggcaggaga |
| | | atcgcttgaa | cccacgaggc |
| 3451 | agtgagctga | gatcatgcca | ctgcacttca |
| | | gcctggatga | cagagctaga |

TABLE 3-continued

| | | | |
|---|---|---|---|
| 3501 | ctccatctca | aaaaaaaaaa | gaatcacaga |
| | | actgaagaca | gtgctggatg |
| 3551 | aggctttggg | gaaccattta | aacctctggg |
| | | cctctgcagg | gaaatcaagc |
| 3601 | ccagcactcc | aacaggacca | gaacacaggc |
| | | agtctccttc | ccagcctagg |
| 3651 | ttctttctct | ccctgccaca | tcaccctggg |
| | | atacctggca | agggccgaat |
| 3701 | aagccaagac | ctccattgtc | tcccatagG |
| | | TATCGGTGAT | GAGCTACAGT |
| 3751 | GCCAAATTTG | CTTCCTGTTT | CTATGGCCCT |
| | | TTCCGgtgag | caggggtggg |
| 3801 | caggggtctg | ctgtgaatcc | ctgcccttg |
| | | gcccaaagct | ggagcccacc |
| 3851 | ctgatgactc | tgctttgcag | GGATGCAGCT |
| | | AAGTCAAGCC | CAGCTTTTGG |
| 3901 | GGACCGCCGC | TGCTACCAGC | TGCCCCCTGG |
| | | AGCACGAGGC | CTGGCTCTCC |
| 3951 | GAGCTGTGgt | gagtgactag | gacttgagcc |
| | | ccaccctcag | cccctccta |
| 4001 | ggcaccaccc | acattatacc | ctcatccctt |
| | | agACCGGGA | TGTACGGGAA |
| 4051 | GGAGCTGACA | TGCTCATGGT | GAAGCCGGGA |
| | | ATGCCCTACC | TGGACATCGT |
| 4101 | GCGGGAGGTA | AAGGACAAGg | tgagcacagg |
| | | tacgaggcaa | aggggctca |
| 4151 | ggggctggg | acagagtttt | ccacagactc |
| | | tggaatctca | gagttggaag |
| 4201 | cagtttgccc | ttaagcatgc | atcctctcct |
| | | cccccttccct | gcccaggaac |
| 4251 | catcgtggcc | ttctatgtcg | gggcttgcac |
| | | gagcctcaaa | cagccctgct |
| 4301 | ttaacagttc | aagagtgggc | caggctgcca |
| | | gccgcagtaa | cccaggacac |
| 4351 | ggggctcaag | atggtcacag | attgagcagg |
| | | ggggaaggga | cgcttccaga |
| 4401 | gccacatcca | ccctccattt | cagcctgtct |
| | | ccctgtctgc | ttccctgcag |
| 4451 | CACCCTGACC | TCCCTCTCGC | CGTGTACCAC |
| | | GTCTCTGGAG | AGTTTGCCAT |
| 4501 | GCTGTGGCAT | GGAGCCCAGG | CCGGGGCATT |
| | | TGATCTCAAG | GCTGCCGTAC |
| 4551 | TGGAGGCCAT | GACTGCCTTC | CGCAGAGCAG |
| | | gtaggcaggc | aagggtgggg |
| 4601 | tgttttgacc | tgcgccacag | ggactgataa |
| | | gcactctgcc | tagatcgggg |
| 4651 | aacgacgtcc | tgagagcttg | ggatcttatt |
| | | ccgggaatta | ctagtgatct |
| 4701 | aaacagacac | acactgagga | agagatatgg |
| | | aactgcagca | tagaacacgg |
| 4751 | cccggtgaag | caagcagagc | ccttcattt |
| | | tggttgtgag | aacgtggcaa |
| 4801 | gccacttctc | tgaacctcag | tgtcctcacc |
| | | cataactgga | taactgggga |
| 4851 | taagatacct | ggtgcgtggt | tgtcctgagg |
| | | attaaatgaa | gtaatatcac |
| 4901 | tccataaagg | ggactcattt | tgttagaatt |
| | | gcacaccagc | atgggaagga |
| 4951 | acttgcctct | tatatttcct | tcactgtgca |
| | | ttttattctt | tggtaaactg |
| 5001 | aggccccaaa | agaggaaatg | acttgcccaa |
| | | gaaatagagt | ttcccaaagc |
| 5051 | tgggctccgt | ctcatgtggt | gtgcccacag |
| | | gctgtgcttc | ttcatggtag |
| 5101 | ccttcttccc | cgcctggcct | tcccatcgca |
| | | gaaggtgtgc | tcagagctga |
| 5151 | tcagcgtccc | cccagcaact | ttctgcatct |
| | | ctcccaacac | agGTGCTGAC |
| 5201 | ATCATCATCA | CCTACTACAC | ACCGCAGCTG |
| | | CTGCAGTGGC | TGAAGGAGGA |
| 5251 | ATGATGGAGA | CAGTGCCAGG | CCCAAGAACT |
| | | AGAACTTTAA | AACGTTCCCG |
| 5301 | GGGCCTCAGA | CAAGTGAAAA | CCAAAGTAAA |
| | | TGCTGCTTTT | AGAACTGTgc |
| 5351 | cctcatgccc | tcttcctgct | cacatgctag |
| | | cggggcccag | cagccctggg |
| 5401 | tggttttgcc | agcatgctaa | ctcttgtaac |
| | | tcgcagctgc | atcctatgag |
| 5451 | ctctcccaag | ctt. | |

2. The method according to claim 1 wherein the sample is analyzed according to a method selected from the group consisting of allele-specific oligonucleotide hybridization, oligonucleotide ligation, ligation amplification, competitive polymerase chain based reaction, and restriction endonuclease digestion.

3. A method for determining altered susceptibility to lead poisoning in a subject comprising the steps of obtaining a biological sample from the subject, extracting DNA from the sample, digesting the DNA with a restriction endonuclease which cleaves DNA in response to the recognition sequence CCGG, and determining whether the DNA sample has been cleaved by the restriction endonuclease within a gene encoding δ-amino levulinate dehydratase.

4. The method according to claim 3, wherein said restriction endonuclease is MspI.

5. The method according to claim 3 further comprising the step of restriction endonuclease digestion with a restriction endonuclease capable of recognizing a second polymorphism in the ALA-D gene.

6. The method according to claim 5 wherein said restriction endonuclease cleaves DNA in response to the recognition sequence GTAC.

7. The method according to claim 5 wherein the second restriction endonuclease is RsaI.

8. The method according to claim 3, further comprising the step of amplification of the DNA encoding the δ-aminolevulinate dehydratase prior to restriction endonuclease cleavage.

9. A method according to claim 8, wherein the DNA amplification method affected is a polymerase chain based reaction utilizing DNA primers having the nucleotide sequences SEQ ID NO: 5 5'AGACAGACATTAGCTCAGTA3' and
SEQ ID NO: 6 5'GGCAAAGACCACGTCCATTC3'.

10. A kit for detecting a polymorphism in a gene encoding δ-aminolevulinate dehydratase in an individual comprising a means for extracting DNA from a sample obtained from an individual, means for detecting the presence of a δ-aminolevulinate dehydratase gene polymorphism in said DNA sample which cleaves DNA in response to the recognition sequence CCGG, and means for amplifying the gene encoding δ-aminolevulinate dehydratase ALA-D2 wherein the amplification means include a polymerase chain reaction utilizing a set of DNA primers having the nucleotide sequences SEQ ID NO 5 5'AGACAGACATTAGCTCAGTA3' and
SEQ ID NO 6 5'GCAAAC=GACCACGTCCATTC3'.

* * * * *

UNITED STATES PATENT AND TRADEMARK OFFICE
CERTIFICATE OF CORRECTION

PATENT NO. : 5,639,607

DATED : June 17, 1997

INVENTOR(S) : Desnick et al.

It is certified that error appears in the above-identified patent and that said Letters Patent is hereby corrected as shown below:

column 1, after line 7, add:  --This invention was supported by National Institute of Health grants DK 34045 and DK 26824. The government may have certain rights in the invention.--

Page 2, 2nd column, line 9, "Seperated" should read --Separated--

Page 2, 2nd column, line 40, "deyhydratase" should read --dehydratase--

Column 4, line 19, "to be" should read --was--

Column 8, last line TABLE 2, insert in the last column under "1208", --1222--

Column 12, line "respectively)" should read --respectively,--

Column 14, line 44, "(MspI$^{31}$)" should read --(MspI$^-$)--

Column 14, line 52, "RsaI$^{31}$ " should read --RsaI$^-$--

Column 17, line 3, "k-AMINO" should read --δ-AMINO--

Column 17, 6th line from the bottom line, "6063" should read --6066--

Column 19, line 2, "k-AMINO" should read --δ-AMINO--

Column 26, 8th line from the bottom line, delete "TABLE 3"

Column 30, line 39 "δ-aminolevulinate" should read --δ-amino levulinate--

Signed and Sealed this

Ninth Day of December, 1997

Attest:

BRUCE LEHMAN

Attesting Officer   Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 20 BASES
        ( B ) TYPE: NUCLEIC ACID
        ( C ) STRANDEDNESS: SINGLE
        ( D ) TOPOLOGY: LINEAR ( i i ) MOLECULE TYPE: OTHER NUCLEIC ACID, SYNTHETIC
        ( A ) DESCRIPTION:

( i i i ) HYPOTHETICAL: NO ( i v ) ANTI-SENSE: NO ( v i i ) IMMEDIATE SOURCE: SYNTHETIC ( x ) PUBLICATION INFORMATION: NONE ( x i ) SEQUENCE DESCRIPTION: SEQ ID NO:1:

AGACAGACATT AGCTCAGTA                                    20

( 2 ) INFORMATION FOR SEQ ID NO: 2:

( i ) SEQUENCE CHARACTERISTICS:
        ( A ) LENGTH: 20 BASES
        ( B ) TYPE: NUCLEIC ACID
        ( C ) STRANDEDNESS: SINGLE
        ( D ) TOPOLOGY: LINEAR ( i i ) MOLECULE TYPE: OTHER NUCLEIC ACID/SYNTHETIC ( i i i ) HYPOTHETICAL: NO ( i v ) ANTI-SENSE: NO ( v i i ) IMMEDIATE SOURCE: SYNTHETIC ( x ) PUBLICATION INFORMATION: NONE ( x i ) SEQUENCE DESCRIPTION: SEQ ID NO: 2:

GGCAAAGACC ACGTCCATTC                                   20

( 2 ) INFORMATION FOR SEQ ID NO: 3:

( i ) SEQUENCE CHARACTERISTICS:
        ( A ) LENGTH: 1222 BASE PAIRS
        ( B ) TYPE: NUCLEIC ACID
        ( C ) STRANDEDNESS: DOUBLE
        ( D ) TOPOLOGY: LINEAR ( i i ) MOLECULE TYPE: cDNA TO mRNA ( i i i ) HYPOTHETICAL: NO ( i v ) ANTI-SENSE: NO ( v i ) ORIGINAL SOURCE: HUMAN
        ( A ) ORGANISM: HUMAN
        ( F ) TISSUE TYPE: LYMPHOBLASTOID CELLS (vii) IMMEDIATE SOURCE:
  (A) LIBRARY: cDNA (ix) FEATURE: GENE PRODUCT IS k-AMINO LEVULINATE
     DEHYDRATASE (x) PUBLICATION INFORMATION: NONE (xi) SEQUENCE DESCRIPTION: SEQ ID NO: 3:

| | |
|---|---|
| GAGACCGGAG CGGGAGACAG CGGTGACAGG AGCAGCGGCC GGGAGCCCTT | 50 |
| AGGGAGGCAG ACAGAGCCTG CAGCCAATGC CCAGGAGCC CTCGGTTCCA | 100 |
| ACCAACTGAT GCCCTGTGC CCACTGGCCC ACGCC ATG CAG CCC CAG | 147 |
| TCC GTT CTG CAC AGC GGC TAC TTC CAC CCA CTA CTT CGG GCC | 189 |
| TGG CAG ACA GCC ACC ACC ACC CTC AAT GCC TCC AAC CTC ATC | 231 |
| TAC CCC ATC TTT GTC ACG GAT GTT CCT GAT GAC ATA CAG CCT | 273 |
| ATC ACC AGC CTC CCA GGA GTG GCC AGG TAT GGT GTG AAC CGG | 315 |
| CTG GAA GAG ATG CTG AGG CCC TTG GTG GAA GAG GGC CTA CGC | 357 |
| TGT GTC TTG ATC TTT GGC GTC CCC AGC AGA GTT CCC AAG GAC | 399 |
| GAG CGG GGT TCC GCA GCT GAC TCC GAG GAG TCC CCA GCT ATT | 441 |
| GAG GCA ATC CAT CTG TTG AGG AAG ACC TTC CCC AAC CTC CTG | 483 |
| GTG GCC TGT GAT GTC TGC CTG TGT CCC TAC ACC TCC CAT GGT | 525 |
| CAC TGC GGG CTC CTG AGT GAA AAC GGA GCA TTC CGG GCT GAG | 567 |
| GAG AGC CGC CAG CGG CTG GCT GAG GTG GCA TTG GCG TAT GCC | 609 |
| AAG GCA GGA TGT CAG GTG GTA GCC CCG TCG ACA TG ATG GAT | 651 |
| GGA CGC GTG AAA GCC ATC AAA GAG GCC CTG ATG GCA CAT GGA | 693 |
| CTT GGC AAC AGG GTA TCG GTG ATG AGC TAC AGT GCC AAA TTT | 735 |
| GCT TCC TGT TTC TAT GGC CCT TTC CGG GAT GCA GCT AAG TCA | 777 |
| AGC CCA GCT TTT GGG GAC CGC CGC TGC TAC CAG CTG CCC CCT | 819 |
| GGA GCA CGA GGC CTG GCT CTC CGA GCT GTG GAC CGG GAT GTA | 861 |
| CGG GAA GGA GCT GAC ATG CTC ATG GTG AAG CCG GGA ATG CCC | 903 |
| TAC CTG GAC ATC GTG CGG GAG GTA AAG GAC AAG CAC CCT GAC | 945 |
| CTC CCT CTC GCC GTG TAC CAC GTC TCT GGA GAG TTT GCC ATG | 987 |
| CTG TGG CAT GGA GCC CAG GCC GGG CA TTT GAT CTC AAG GCT | 1029 |
| GCC GTA CTG GAG GCC ATG ACT GCC TTC CGC AGA GCA GGT GCT | 1071 |
| GAC ATC ATC ATC ACC TAC TAC ACA CCG CAG CTG CTG CAG TGG | 1113 |
| CTG AAG GAG GAA TGA TGGAGACAGT GCCAGGCCCA AGAACTAGAA | 1158 |
| CTTTAAAACG TTCCCGGGGC CTCAGACAAG TGAAAACCAA AGTAAATGCT | 1208 |
| GCTTTTAGAA CTGT | 1222 |

(2) INFORMATION FOR SEQ ID NO: 4:

(i) SEQUENCE CHARACTERISTICS:
    (A) LENGTH: 6063
    (B) TYPE: NUCLEIC ACID
    (C) STRANDEDNESS: DOUBLE
    (D) TOPOLOGY: LINEAR (ii) MOLECULE TYPE: GENOMIC DNA (iii) HYPOTHETICAL: YES ( i v ) ANTI-SENSE: NO ( i x ) FEATURE: GENE PRODUCT IS k-AMINO LEVULINATE DEHYDRATASE ( x ) PUBLICATION INFORMATION: NONE ( x i ) SEQUENCE DESCRIPTION: SEQ ID NO: 4:

| | | | | |
|---|---|---|---|---|
| GAGACCATCC | TGGGAAGCAT | GGCAAGACCT | CCATCTCTAC | AAAAAATTCG | 50
| AAAATTAGCT | GGATGTTGTG | GTGCACACCT | GCAGTCCCAG | CTACTTGGGA | 100
| GGCTGAGTTG | GGAGAAACAG | TTGAGCCCGG | GAGGTCAAGG | CTGCAGTGAG | 150
| TCGAGATTGC | ACCACTGCAC | TCCAGCCTGG | GCGACAGAGA | CCCTGTGTGA | 200
| AAAAAAAAAA | AAGAAGAGAA | TTTTTTTTAA | ACAGTCATTG | CTTGCTCAGA | 250
| TGTTTACTTT | AAAGATAAT | AATGAACAAG | AAGCAGTCAC | ATAAAATACA | 300
| AGCCCAAATT | TTATATCATT | AGATTCTGAT | TGTCATGAAA | GTTCTAAAG | 350
| ACTTACTTTC | ATTTCTCAAC | TTACCTTGTT | GACCAGCAGG | GATTGGTGAA | 400
| CCAGGCTGTG | AGTAGCATTG | GGCTAGAGAG | AGGGGAGGCA | GGAATCTAGA | 450
| AGAGCTGTTT | TCCAGATGTG | ACCATCTCCT | GAGGACAGGG | ACCATGTCCT | 500
| ATGTGCCACC | CATCACCCCC | CACAGACAGA | GCCTGCAGCC | AATGCCCCAG | 550
| GAGCCCTCGG | TTCCAACCAA | CTGATGCCCC | TGTGCCCACT | GGCCACGCC | 600

| | | | | | | | | | | | | | |
|---|---|---|---|---|---|---|---|---|---|---|---|---|---|
| ATG | CAG | CCC | CAG | TCC | GTT | CTG | CAC | AGC | GGC | TAC | TTC | CAC | CCA | 642
| CTA | CTT | CGG | GCC | TGG | CAG | ACA | GCC | ACC | ACC | ACC | CTC | AAT | GCC | 684
| TCC | AAC | CTC | ATC | TAC | CCC | ATC | TTT | GTC | AC | | | | | 723

| | | | | |
|---|---|---|---|---|
| | | | | GTGAGTCTCC |
| AAGAATGGGC | CAGGCCTCTG | CTCTGCTGGT | TGGGGTTGGG | GTTGGGGAGG | 773
| GAGTGTTGAC | TGGAGCGGGC | ATCAGTATGG | CTGGGGGTGG | CAAAGTGAGC | 823
| TGTCAGCTTG | AAATTCAAGG | CACTGGAAGC | AGGCTACTTG | GATTAAGGAC | 873
| AGGAATCTTA | GGAACAAAAC | AAACTTTGAA | AGAACTCATT | CATCCCATTT | 923
| GGAAAATTAG | AAGAATAACC | CTTGCCTGCC | ATCCTGAGCT | CTTGCAGTAA | 973
| GACAGAAGCT | GAGAAGGTGC | TCTGTACATT | GTAAAGTGCT | ATGTACCTGT | 1023
| AAGAGATGGC | AGTCATTGAG | GCTGGGCACG | GTGGCTCACG | CCTGTAATCC | 1073
| CAGCACTTTG | GGAGGCTGAG | GCAGGCGGAT | CACGAGGTCA | GGAGATCGAG | 1123
| ACCATCCTGG | CTAATATGGT | GAAACCCTGT | CTCTACTAAA | AACACAAAGA | 1173
| AATTAGCCAG | GCGTGGTGGC | GGGTGCCTGT | AGTCCCAGCT | ACTTGGGAGG | 1223
| CTGAGGCAGG | AGAATGGCGT | GAACCCGGGA | GGCGGAGCTT | GCAGTGAGCC | 1273
| GAGATTGCAC | CACTTCACTC | CAGCCTGGGC | GACAGAGCCA | GACTCCATCT | 1323
| CAAAAAAAAA | AAAAAAAAA | AGAGATGGCA | ATCGTGATTG | TTAATAATAA | 1373
| TGCAGACATT | TACTGAGTAC | TTACTATCTA | CCAGGTACTA | TGCTAAGCAC | 1423
| CTACACACAT | TATCTCATTC | AATTCTGAGA | GCATTTGTAT | GAAGAAGGAG | 1473
| TAGCTATCCT | CTAGAACATC | AGCTCCATGA | GGGCAGGGAT | GTTTGTCTAT | 1523
| TTTGTTCACT | GTTGTATCAT | CAGGGCCTAG | AACAGTACTT | GGCACATAAT | 1573
| AAGTACTCAA | TAAATATTTG | TTGAATGAAT | GAATTAACCA | CGCATGATAT | 1623
| AGATGAAGGC | CTAAGGCTCA | AAGAGATGAT | AGAACTTGGC | CACGGTCACC | 1673
| CAGGCAGTAA | GTGGCTGGGA | TAGAAAGCAA | GGACCTGCCA | AATTCAGAGT | 1723
| CCAAGTTCTT | AACCACTTAA | TTCCTTCCTG | TAATTACCGT | TCTTTTAGTA | 1773

```
CAGTTGCTAG TGTTGTCACT GTTATTCTTG TTGTTCCTAT TATTATTTCA        1823
GGCCCTGGGC TTGGCCAGGC AGGGAAGCCA GACACTGGAT CCCATCCTCC        1873
TCCCACCATC TCCACTTCCA TATTTCTTTC CTGCTTCCCA ACCATCCCTC        1923
TCAGTCGCCC CCGCACCACT GGCCCTTCCC ACAGCTACCA ATCCATATCC        1973
CACCCCCGCT CTTGCAG GG ATG TTC CTG ATG ACA TAC AGC CTA         2016
TCA CCA GCC TCC CAG GAG TGG CCA G GTAGGAGACG TGGAGTTGGG       2061
GGGCCAGCGG GTGGTGGAGG GAGAGATTCC ACAGGTGGAA GTGCTGGGAG        2111
GCAGAAGCAG ACCTAGGAAG TAGAAGATGC GGACAGACAG ACATTAGCTC        2161
AGTAGAGGAA AGGGTTTCCC CGGGGCCAGA GCTGTTCCAC AGTGGAAGGG        2211
GCAGCCCCAT AAAGTAAAGA CTACCCATC ACCCGAGACG TCGTGGCAGA         2261
GGCTGTTGCA GAAGGGAGCT GAACTGCAGA TGGGAGTTCA AAAGAGGGC         2311
CTCGAAGGAG CCTTCCACAG CCGAATTCCG GAGCTCTGCT ACTCAGGGCC        2361
TCAGTCTTCC CTCCTATTTA GTGGATGCAT CCCTGCCCCT TCTGTCCTGG        2411
GGGCTTGAGC CCTCCTGGTG CCATATGCAG CTTGGTTTCT AACAGAGGCA        2461
CACAGTGTGG TGGGTCCGG AGGACCGTTG CCTGGGACCT GCCTTCCTTC         2511
AACCCCTCTA CCCACACCCA CACAG GT ACG GTG TGA ACC GGC TGG        2556
AAG AGA TGC TGA GGC CCT TGG TGG AAG AGG GCC TAC GCT GTG       2598
TCT TGA TCT TTG GCG TCC CCA GCA GAG TTC CCA AG                2633
GTGAAGAATC AAAGGAAGGG CTAAGAAGGG AGGTTGCCTC ACGCCCGTAA        2683
TCCCAGCACT TTGGGAGGCC AAAGTGGGTG GATCACTTGA GCCCAGGATT        2733
TTGAGACCAG CCTGGACAAC ATGGCAAAAC CCATCTCTAC AAAAAATACA        2783
AAAGTTAGCT GGGTGTGGGG GTATGTGCCT GTAGTCCCAG CTACTCGGGA        2833
GGTGGAGAGG TGGGAGGATT GCTTGAGCCC AGAAAGTCGA GGCTGCAGTG       2883
AGCCAAAATC GCGCCAGTGC ACTCTAGCCT GGGTGACAGA GCAAGACCCT        2933
GTCTCCAATA CAAACAGAAA AAGGAAGGGA GGTTGGGCAA AGGTGGACTG       2983
AGGGTCCACA CTGACTGCAC CCTCACTCCC ACATTGTGCT GGCCCTGGGG       3033
CCACAGGTGA ATGGACGTGG TCTTTGCCCT TAAGTCAGCA CCCATGTAGG       3083
GTCGGTCCTC TGTGCTTCCT TATCCAGGGG CTGTGATGAT GAAGGAAGGA       3133
GAAGGCCAGG GCTATGCTCT GTGATGGCTG TCATCCTGCC TTCCAAAGCT        3183
ACATGTAATA GACACACTGC TTTGTCCCTC CCTGCCCCT AG G ACG           3229
AGC GGG GTT CCG CAG CTG ACT CCG AGG AGT CCC CAG CTA TTG       3271
AGG CAA TCC ATC TGT TGA GGA AGA CCT TCC CCA ACC TCC TGG       3313
TGG CCT GTG ATG TCT GCC TGT GTC CCT ACA CCT CCC ATG GTC       3355
ACT GCG GTGAGTTCCC TCCTCCCAC CAGCCCTGCT GCCACCCACA           3401
CTCCTACTGC CCACTTCTCA ACAGGGTGGG GACAGCCAGG GCCCAAGGTG       3451
CTCCCCAAAA CCCAGTCATC TGTCCTGAAG GGC TCC TGA GTG AAA          3496
ACG GAG CAT TCC GGG CTG AGG AGA GCC GCC AGC GGC TGG CTG       3538
AGG TGG CAT TGG CGT ATG CCA AGG CAG GTGAGTGAAC               3575
CACCAGCAGG GATGGGCACC TCTGGGTCAG GAGGTGGCAG AGTGGCTAG        3624
GAGGGCCCCA GAGTTCTGAA GGCCACCCTC TGCCCCCAG GAT GTC AGG       3673
```

| | |
|---|---|
| TGG TAG CCC CGT CGG ACA TGA TGG ATG GAC GCG TGG AAG CCA | 3715 |
| TCA AAG AGG CCC TGA TGG CAC ATG GAC TTG GCA ACA GG | 3753 |
| GTAAGGGCAG GGAATGCAGC ACAGGGCTGG CAGGAGATAG TCTGCACCAG | 3803 |
| CCCTGCCCCC GTGTCTGCTA AGAATCACAG AACTGCCGGG CGTGTTGGCT | 3853 |
| CACACCTGTA GTCCAGCAC TTTGGGAGGC TGAGGCAGGT AGATCACTTG | 3903 |
| AGGTCAGGGG TTCAAGACCA GCCTGGCCAA CATGGTGAAA CCCCATCTCT | 3953 |
| ACTAAAAACA CAAAAATTAG CTGGGCGTGG TGGCAGGCGC CTGCAATCCC | 4003 |
| AGCTACTGGG GAGGCTGAGG CAGGAGAATC GCTTGAACCC ACGAGGCAGT | 4053 |
| GAGCTGAGAT CATGCCACTG CACTTCAGCC TGGATGACAG AGCTAGACTC | 4103 |
| CATCTCAAAA AAAAAAGAA TCACAGAACT GAAGACAGTG CTGGATGAGG | 4153 |
| CTTTGGGGAA CCATTTAAAC CTCTGGGCCT CTGCAGGGAA ATCAAGCCCA | 4203 |
| GCACTCCAAC AGGACCAGAA CACAGGCAGT CTCCTTCCCA GCCTAGGTTC | 4253 |
| TTTCTCTCCC TGCCACATCA CCCTGGGATA CCTGGCAAGG GCCGAATAAG | 4303 |
| CCAAGACCTC CATTGTCTCC CCATAG G TAT CGG TGA TGA GCT | 4345 |
| ACA GTG CCA AAT TTG CTT CCT GTT TCT ATG GCC CTT TCC G | 4385 |
| GTGAGCAGGG GTGGGCAGGG GTCTGCTGTG AATCCCTGCC CTTTGGCCCA | 4435 |
| AAGCTGGAGC CCACCCTGAT GACTCTGCTT TGCAG GG ATG CAG CTA | 4481 |
| AGT CAA GCC CAG CTT TTG GGG ACC GCC GCT GCT ACC AGC TGC | 4523 |
| CCC CTG GAG CAC GAG GCC TGG CTC TCC GAG CTG TG | 4558 |
| GTGAGTGACT AGGACTTGAG CCCCACCCTC AGCCCCTCC TAGGCACCAC | 4608 |
| CCACATTATA CCCTCATCCC TTAG G ACC GGG ATG TAC GGG AAG | 4651 |
| GAG CTG ACA TGC TCA TGG TGA AGC CGG GAA TGC CCT ACC TGG | 4693 |
| ACA TCG TGC GGG AGG TAA AGG ACA AG GTGAGCACAG | 4729 |
| GTACGAGGCA AAGGGGGCTC AGGGGGCTGG GACAGAGTTT TCCACAGACT | 4779 |
| CTGGAATCTC AGAGTTGGAA GCAGTTTGCC CTTAAGCATG CATCCTCTCC | 4829 |
| TCCCCTTCCC TGCCCAGGAA CCATCGTGGC CTTCTATGTC GGGGCTTGCA | 4879 |
| CGAGCCTCAA ACAGCCCTGC TTTAACAGTT CAAGAGTGGG CCAGGCTGCC | 4929 |
| AGCCGCAGTA ACCCAGGACA CGGGGCTCAA GATGGTCACA GATTGAGCAG | 4979 |
| GGGGGAAGGG ACGCTTCCAG AGCCACATCC ACCCTCCATT TCAGCCTGTC | 5029 |
| TCCCTGTCTG CTTCCCTGCA G C ACC CTG ACC TCC CTC TCG CCG | 5072 |
| TGT ACC ACG TCT CTG GAG AGT TTG CCA TGC TGT GGC ATG | 5111 |
| GAG CCC AGG CCG GGG CAT TTG ATC TCA AGG CTG CCG TAC | 5150 |
| TGG AGG CCA TGA CTG CCT TCC GCA GAG CAG GTAGGCAGGC | 5190 |
| AAGGGTGGGG TGTTTTGACC TGCGCCACAG GGACTGATAA GCACTCTGCC | 5240 |
| TAGATCGGGG AACGACGTCC TGAGAGCTTG GGATCTTATT CCGGGAATTA | 5290 |
| CTAGTGATCT AAACAGACAC ACACTGAGGA AGAGATATGG AACTGCAGCA | 5340 |
| TAGAACACGG CCCGGTGAAG CAAGCAGAGC CCTTCATTTT TGGTTGTGAG | 5390 |
| AACGTGGCAA GCCACTTCTC TGAACCTCAG TGTCCTCACC CATAACTGGA | 5440 |
| TAACTGGGA TAAGATACCT GGTGCGTGGT TGTCCTGAGG ATTAAATGAA | 5490 |
| GTAATATCAC TCCATAAAGG GGACTCATTT TGTTAGAATT GCACACCAGC | 5540 |

| | | | | |
|---|---|---|---|---|
| ATGGGAAGGA | ACTTGCCTCT | TATATTTCCT | TCACTGTGCA | TTTTATTCTT | 5590 |
| TGGTAAACTG | AGGCCCCAAA | AGAGGAAATG | ACTTGCCCAA | GAAATAGAGT | 5640 |
| TTCCCAAAGC | TGGGCTCCGT | CTCATGTGGT | GTGCCCACAG | GCTGTGCTTC | 5690 |
| TTCATGGTAG | CCTTCTTCCC | CGCCTGGCCT | TCCCATCGCA | GAAGGTGTGC | 5740 |
| TCAGAGCTGA | TCAGCGTCCC | CCCAGCAACT | TTCTGCATCT | CTCCCAACAC | 5790 |
| AG GTG CTG | ACA TCA TCA | TCA CCT ACT | ACA CAC CGC | AGC TGC | 5831 |
| TGC AGT GGC | TGA AGG AGG | AAT GAT GGA | GAC AGT GCC | AGG CCC | 5873 |
| AAG AAC TAG | AAC TTT AAA | ACG TTC CCG | GGG CCT CAG | ACA AGT | 5915 |
| GAA AAC CAA | AGT AAA TGC | TGC TTT TAG | AAC TGT GCC | CTCATGC | 5958 |
| CCTCTTCCTG | CTCACATGCT | AGCGGGGCCC | AGCAGCCTG | GGTGGTTTTG | 6008 |
| CCAGCATGCT | AACTCTTGTA | ACTCGCAGCT | GCATCCTATG | AGCTCTCCA | 6058 |
| AGCTT | | | | | 6063 |

( 2 ) INFORMATION FOR SEQ ID NO: 5:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: LINEAR ( i i ) MOLECULE TYPE: OTHER/SYNTHETIC ( i i i ) HYPOTHETICAL: NO ( i v ) ANTI-SENSE: NO ( x ) PUBLICATION INFORMATION: NONE ( x i ) SEQUENCE DESCRIPTION: SEQ ID NO:5:

AGACAGACAT TAGCTCAGTA                20

( 2 ) INFORMATION FOR SEQ ID NO: 6:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: LINEAR ( i i ) MOLECULE TYPE: OTHER/SYNTHETIC ( i i i ) HYPOTHETICAL: NO ( i v ) ANTI-SENSE: NO ( x ) PUBLICATION INFORMATION: NONE ( x i ) SEQUENCE DESCRIPTION: SEQ ID NO: 6:

GGCAAAGACC ACGTCCATTC                20